(12) United States Patent
Telfort et al.

(10) Patent No.: US 9,192,351 B1
(45) Date of Patent: Nov. 24, 2015

(54) ACOUSTIC RESPIRATORY MONITORING SENSOR WITH PROBE-OFF DETECTION

(75) Inventors: Valery G. Telfort, Laval (CA); Dimitar Dimitrov, Quebec (CA); Mark Wylie, Dorval (CA)

(73) Assignee: MASIMO CORPORATION, Irvine, CA (US)

( * ) Notice: Subject to any disclaimer, the term of this patent is extended or adjusted under 35 U.S.C. 154(b) by 290 days.

(21) Appl. No.: 13/554,929

(22) Filed: Jul. 20, 2012

Related U.S. Application Data

(60) Provisional application No. 61/510,926, filed on Jul. 22, 2011.

(51) Int. Cl.
*A61B 7/00* (2006.01)
*A61B 7/04* (2006.01)
(Continued)

(52) U.S. Cl.
CPC . *A61B 7/003* (2013.01); *A61B 7/04* (2013.01); *A61B 5/0006* (2013.01); *A61B 5/0205* (2013.01);
(Continued)

(58) Field of Classification Search
CPC ........ A61B 7/003; A61B 7/04; A61B 5/0006; A61B 5/02438; A61B 5/02444; A61B 5/08; A61B 5/0816; A61B 5/145; A61B 5/4818; A61B 5/6822; A61B 5/6833; A61B 5/721; A61B 5/6843; A61B 5/7203; A61B 2560/0412; A61B 2562/0204; A61B 2562/182; A61B 2562/227; A61B 5/0205; Y10T 29/49005; H04R 1/46
USPC ............. 600/586, 301; 381/67, 150; 342/451, 342/463; 257/254, 416; 310/313 R, 322, 310/334; 340/856.4, 575
See application file for complete search history.

(56) References Cited

U.S. PATENT DOCUMENTS

| | | |
|---|---|---|
| 3,682,161 A | 8/1972 | Alibert |
| 3,951,230 A | 4/1976 | Littmann |

(Continued)

FOREIGN PATENT DOCUMENTS

| | | |
|---|---|---|
| CA | 2490438 | 4/2003 |
| CA | 2262236 | 4/2008 |

(Continued)

OTHER PUBLICATIONS

U.S. Appl. No. 10/180,518, filed Jun. 27, 2002, Lanzo et al.
(Continued)

*Primary Examiner* — Brian Szmal
(74) *Attorney, Agent, or Firm* — Knobbe, Martens, Olson & Bear, LLP

(57) ABSTRACT

An acoustic sensor configured to non-invasively detect acoustic vibrations associated with a medical patient. The acoustic vibrations are indicative of one or more physiological parameters of the medical patient. The acoustic sensor can include a sensor support and at least one sound sensing membrane supported by the sensor support. The membrane can be configured to detect acoustic vibrations associated with a medical patient. The membrane may also be configured to produce a membrane signal corresponding to the acoustic vibrations when the acoustic sensor is attached to the medical patient. The acoustic sensor can also include a probe-off assembly supported by the sensor support. The probe-off assembly can be configured to produce a probe-off signal responsive to attachment of the acoustic sensor to the medical patient and detachment of the acoustic sensor from the medical patient.

27 Claims, 14 Drawing Sheets

(51) Int. Cl.
   *A61B 5/08* (2006.01)
   *A61B 5/00* (2006.01)
   *A61B 5/024* (2006.01)
   *A61B 5/0205* (2006.01)
   *A61B 5/145* (2006.01)
   *H04R 1/46* (2006.01)

(52) U.S. Cl.
   CPC ......... *A61B 5/02438* (2013.01); *A61B 5/02444* (2013.01); *A61B 5/08* (2013.01); *A61B 5/0816* (2013.01); *A61B 5/145* (2013.01); *A61B 5/4818* (2013.01); *A61B 5/6822* (2013.01); *A61B 5/6833* (2013.01); *A61B 5/6843* (2013.01); *A61B 5/721* (2013.01); *A61B 5/7203* (2013.01); *A61B 2560/0412* (2013.01); *A61B 2562/0204* (2013.01); *A61B 2562/182* (2013.01); *A61B 2562/227* (2013.01); *H04R 1/46* (2013.01); *Y10T 29/49005* (2015.01)

(56) References Cited

U.S. PATENT DOCUMENTS

| | | |
|---|---|---|
| 4,127,749 A | 11/1978 | Atoji et al. |
| 4,254,302 A | 3/1981 | Walshe |
| 4,326,143 A | 4/1982 | Guth et al. |
| 4,413,202 A | 11/1983 | Krempl et al. |
| 4,537,200 A | 8/1985 | Widrow |
| 4,576,179 A | 3/1986 | Manus et al. |
| 4,578,613 A | 3/1986 | Posthuma de Boer et al. |
| 4,634,917 A | 1/1987 | Dvorsky et al. |
| 4,672,976 A | 6/1987 | Kroll |
| 4,805,633 A | 2/1989 | Kotani et al. |
| 4,827,943 A | 5/1989 | Bornn et al. |
| 4,884,809 A | 12/1989 | Rowan |
| 4,924,876 A | 5/1990 | Cameron |
| 4,947,859 A | 8/1990 | Brewer et al. |
| 4,960,118 A | 10/1990 | Pennock |
| 4,960,128 A | 10/1990 | Gordon et al. |
| 4,964,408 A | 10/1990 | Hink et al. |
| 4,982,738 A | 1/1991 | Griebel |
| 5,003,605 A | 3/1991 | Phillipps et al. |
| 5,033,032 A | 7/1991 | Houghtaling |
| 5,036,857 A | 8/1991 | Semmlow et al. |
| 5,041,187 A | 8/1991 | Hink et al. |
| 5,069,213 A | 12/1991 | Polczynski |
| 5,078,151 A | 1/1992 | Laballery |
| 5,140,992 A | 8/1992 | Zuckerwar et al. |
| 5,143,078 A | 9/1992 | Mather et al. |
| 5,163,438 A | 11/1992 | Gordon et al. |
| 5,269,314 A | 12/1993 | Kendall et al. |
| 5,278,627 A | 1/1994 | Aoyagi et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,406,952 A | 4/1995 | Barnes et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,448,996 A | 9/1995 | Bellin et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,539,831 A | 7/1996 | Harley |
| 5,561,275 A | 10/1996 | Savage et al. |
| 5,562,002 A | 10/1996 | Lalin |
| 5,564,108 A | 10/1996 | Hunsaker et al. |
| 5,578,799 A | 11/1996 | Callahan et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,738,106 A | 4/1998 | Yamamori et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,812,678 A | 9/1998 | Scalise et al. |
| 5,823,950 A | 10/1998 | Diab et al. |
| 5,825,895 A | 10/1998 | Grasfield et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,912,656 A | 6/1999 | Tham et al. |
| 5,919,134 A | 7/1999 | Diab |
| 5,934,925 A | 8/1999 | Tobler et al. |
| 5,940,182 A | 8/1999 | Lepper, Jr. et al. |
| 5,977,538 A | 11/1999 | Unger et al. |
| 5,989,193 A | 11/1999 | Sullivan |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,083,156 A | 7/2000 | Lisiecki |
| 6,088,607 A | 7/2000 | Diab et al. |
| 6,106,481 A | 8/2000 | Cohen |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,168,568 B1 | 1/2001 | Gavriely |
| 6,184,521 B1 | 2/2001 | Coffin, IV et al. |
| 6,206,830 B1 | 3/2001 | Diab et al. |
| 6,210,344 B1 | 4/2001 | Perin et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,248,083 B1 | 6/2001 | Smith et al. |
| 6,253,097 B1 | 6/2001 | Aronow et al. |
| 6,256,523 B1 | 7/2001 | Diab et al. |
| 6,261,237 B1 | 7/2001 | Swanson et al. |
| 6,263,222 B1 | 7/2001 | Diab et al. |
| 6,275,594 B1 | 8/2001 | Senoo et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,295,365 B1 | 9/2001 | Ota |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |

(56) References Cited

U.S. PATENT DOCUMENTS

| | | |
|---|---|---|
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,415,033 B1 | 7/2002 | Halleck et al. |
| 6,423,013 B1 | 7/2002 | Bakker et al. |
| 6,430,437 B1 | 8/2002 | Marro |
| 6,430,525 B1 | 8/2002 | Weber et al. |
| 6,438,238 B1 | 8/2002 | Callahan |
| 6,463,311 B1 | 10/2002 | Diab |
| 6,470,199 B1 | 10/2002 | Kopotic et al. |
| 6,486,588 B2 | 11/2002 | Doron et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,517,497 B2 | 2/2003 | Rymut et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,816,744 B2 | 11/2004 | Garfield et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,937,736 B2 | 8/2005 | Toda |
| 6,939,305 B2 | 9/2005 | Flaherty et al. |
| 6,943,348 B1 | 9/2005 | Coffin IV |
| 6,950,687 B2 | 9/2005 | Al-Ali |
| 6,954,971 B1 | 10/2005 | Bryant et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,035,684 B2 | 4/2006 | Lee |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,110,804 B2 | 9/2006 | Baumer et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,246,069 B1 | 7/2007 | O'Hanlon et al. |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,270,126 B2 | 9/2007 | Wallace et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,148 B2 | 4/2008 | Narimatsu |
| 7,368,855 B2 | 5/2008 | Orten |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,469,158 B2 | 12/2008 | Cutler et al. |
| 7,471,969 B2 | 12/2008 | Diab et al. |
| 7,471,971 B2 | 12/2008 | Diab et al. |
| 7,483,729 B2 | 1/2009 | Al-Ali et al. |

(56) References Cited

U.S. PATENT DOCUMENTS

| | | |
|---|---|---|
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,515,044 B2 | 4/2009 | Welch et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| 7,662,105 B2 | 2/2010 | Hatlestad |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,783,056 B2 | 8/2010 | Wilmink |
| 7,791,155 B2 | 9/2010 | Diab |
| 7,801,581 B2 | 9/2010 | Diab |
| 7,806,226 B2 | 10/2010 | Drummond et al. |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,860,553 B2 | 12/2010 | Govari et al. |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,940,937 B2 | 5/2011 | Smith |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,976,480 B2 | 7/2011 | Grajales et al. |
| 7,988,637 B2 | 8/2011 | Diab |
| 7,988,688 B2 | 8/2011 | Webb et al. |
| 7,990,382 B2 | 8/2011 | Kiani |
| 7,991,165 B2 | 8/2011 | Kassal et al. |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,092,396 B2 | 1/2012 | Bagha et al. |
| 8,108,039 B2 | 1/2012 | Saliga et al. |
| RE43,169 E | 2/2012 | Parker |
| 8,118,620 B2 | 2/2012 | Al-Ali et al. |
| 8,121,673 B2 | 2/2012 | Tran |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali et al. |
| 8,229,533 B2 | 7/2012 | Diab et al. |
| 8,233,955 B2 | 7/2012 | Al-Ali et al. |
| 8,241,223 B2 | 8/2012 | Gavriely et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,291 B2 | 9/2012 | Bridger et al. |
| 8,265,723 B1 | 9/2012 | Weber et al. |
| 8,274,360 B2 | 9/2012 | Sampath et al. |
| 8,275,140 B2 | 9/2012 | Smith |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| 8,320,576 B1 | 11/2012 | Abbruscato |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,396,228 B2 | 3/2013 | Bilan |
| 8,399,822 B2 | 3/2013 | Al-Ali |
| 8,401,602 B2 | 3/2013 | Kiani |
| 8,403,865 B2 | 3/2013 | Halperin et al. |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,449,469 B2 | 5/2013 | Banet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,517,981 B2 | 8/2013 | Zornow |

(56) References Cited

U.S. PATENT DOCUMENTS

| | | |
|---|---|---|
| 8,523,781 B2 | 9/2013 | Al-Ali |
| 8,526,665 B2 | 9/2013 | Lutz et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,595 B2 | 2/2014 | Basinger |
| 8,641,631 B2 | 2/2014 | Sierra et al. |
| 8,652,060 B2 | 2/2014 | Al-Ali et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| RE44,823 E | 4/2014 | Parker |
| 8,690,799 B2 | 4/2014 | Telfort et al. |
| 8,702,627 B2 | 4/2014 | Telfort et al. |
| 8,715,206 B2 | 5/2014 | Telfort et al. |
| 8,755,535 B2 | 6/2014 | Telfort et al. |
| 8,771,204 B2 | 7/2014 | Telfort et al. |
| 8,790,268 B2 | 7/2014 | Al-Ali et al. |
| 8,801,613 B2 | 8/2014 | Al-Ali et al. |
| 8,821,415 B2 | 9/2014 | Al-Ali et al. |
| 8,870,792 B2 | 10/2014 | Al-Ali et al. |
| 2002/0161291 A1 | 10/2002 | Kiani et al. |
| 2002/0193670 A1 | 12/2002 | Garfield et al. |
| 2003/0015368 A1 | 1/2003 | Cybulski et al. |
| 2004/0133087 A1 | 7/2004 | Ali et al. |
| 2004/0158162 A1 | 8/2004 | Narimatsu |
| 2004/0167416 A1 | 8/2004 | Lee |
| 2004/0228494 A1 | 11/2004 | Smith |
| 2005/0272987 A1 | 12/2005 | Kiani-Azarbayjany et al. |
| 2005/0283059 A1 | 12/2005 | Iyer et al. |
| 2006/0047215 A1 | 3/2006 | Newman et al. |
| 2006/0144397 A1 | 7/2006 | Wallace et al. |
| 2006/0184052 A1 | 8/2006 | Iwasawa |
| 2006/0198533 A1 | 9/2006 | Wang |
| 2006/0238333 A1 | 10/2006 | Welch et al. |
| 2007/0049837 A1 | 3/2007 | Shertukde et al. |
| 2007/0058818 A1* | 3/2007 | Yoshimine ............... 381/67 |
| 2007/0135725 A1 | 6/2007 | Hatlestad |
| 2007/0173730 A1 | 7/2007 | Bikko |
| 2007/0185397 A1 | 8/2007 | Govari et al. |
| 2007/0282174 A1 | 12/2007 | Sabatino |
| 2007/0282212 A1 | 12/2007 | Sierra et al. |
| 2008/0039735 A1 | 2/2008 | Hickerson |
| 2008/0076972 A1 | 3/2008 | Dorogusker et al. |
| 2008/0077198 A1 | 3/2008 | Webb et al. |
| 2008/0077435 A1 | 3/2008 | Muradia |
| 2008/0097249 A1 | 4/2008 | Pool et al. |
| 2008/0137876 A1 | 6/2008 | Kassal et al. |
| 2008/0188733 A1 | 8/2008 | Al-Ali et al. |
| 2008/0219464 A1 | 9/2008 | Smith |
| 2009/0018429 A1 | 1/2009 | Saliga et al. |
| 2009/0093687 A1 | 4/2009 | Telfort et al. |
| 2009/0170664 A1 | 7/2009 | Shirasaki et al. |
| 2009/0187065 A1 | 7/2009 | Basinger |
| 2009/0299157 A1 | 12/2009 | Telfort et al. |
| 2009/0316925 A1 | 12/2009 | Eisenfeld et al. |
| 2010/0090901 A1* | 4/2010 | Smith et al. ............... 342/451 |
| 2010/0094096 A1 | 4/2010 | Petruzzelli et al. |
| 2010/0274099 A1 | 10/2010 | Telfort et al. |
| 2011/0034831 A1 | 2/2011 | Christensen et al. |
| 2011/0125060 A1 | 5/2011 | Telfort et al. |
| 2011/0172551 A1 | 7/2011 | Al-Ali |
| 2011/0172561 A1 | 7/2011 | Kiani et al. |
| 2011/0196211 A1 | 8/2011 | Al-Ali et al. |
| 2011/0209915 A1 | 9/2011 | Fetcher et al. |
| 2011/0213271 A1 | 9/2011 | Telfort et al. |
| 2011/0213272 A1 | 9/2011 | Telfort et al. |
| 2011/0213273 A1 | 9/2011 | Telfort et al. |
| 2011/0213274 A1 | 9/2011 | Telfort et al. |
| 2011/0224567 A1 | 9/2011 | Al-Ali |
| 2011/0288431 A1 | 11/2011 | Alshaer et al. |
| 2012/0232427 A1 | 9/2012 | Bakema et al. |
| 2012/0302920 A1 | 11/2012 | Bridger et al. |
| 2013/0090567 A1 | 4/2013 | Al Ali et al. |
| 2014/0081175 A1 | 3/2014 | Telfort |
| 2014/0303520 A1 | 10/2014 | Telfort et al. |
| 2014/0309559 A1 | 10/2014 | Telfort et al. |

FOREIGN PATENT DOCUMENTS

| | | |
|---|---|---|
| CN | 201497610 | 6/2010 |
| CN | 202005761 | 10/2011 |
| EP | 0716628 | 12/1998 |
| EP | 0659058 | 1/1999 |
| EP | 0956820 A1 | 11/1999 |
| EP | 1207536 | 5/2002 |
| EP | 1518442 | 3/2005 |
| EP | 2014234 | 1/2009 |
| EP | 2391273 | 12/2011 |
| EP | 2488106 | 8/2012 |
| EP | 2488978 | 8/2012 |
| EP | 2710959 | 3/2014 |
| EP | 2765909 | 8/2014 |
| FR | 2 847 796 | 6/2004 |
| GB | 2358546 | 11/1999 |
| JP | S53-094482 A | 8/1978 |
| JP | S56-031742 A | 3/1981 |
| JP | 60059900 | 4/1985 |
| JP | 6214898 | 1/1987 |
| JP | H04-317637 A | 11/1992 |
| JP | H07-152553 A | 6/1995 |
| JP | 01-309872 | 6/1998 |
| JP | 10-155755 | 6/1998 |
| JP | 2001-50713 | 5/1999 |
| JP | 2003-329719 | 11/2003 |
| JP | 2005-522292 A | 7/2005 |
| JP | 2005-531230 A | 10/2005 |
| JP | 2012-513872 | 12/2009 |
| JP | 2013-508029 | 10/2010 |
| JP | 2013-508030 | 10/2010 |
| NO | 20040819 | 4/2003 |
| WO | WO 94/05207 | 3/1994 |
| WO | WO 94/13207 | 6/1994 |
| WO | WO 95/29632 | 11/1995 |
| WO | WO 99/53277 | 10/1999 |
| WO | WO 00/10462 | 3/2000 |
| WO | WO 01/34033 | 5/2001 |
| WO | WO 01/78059 | 10/2001 |
| WO | WO 01/87005 | 11/2001 |
| WO | WO 01/97691 | 12/2001 |
| WO | WO 02/03042 | 1/2002 |
| WO | WO 02/24067 | 3/2002 |
| WO | WO 03/058646 | 7/2003 |
| WO | WO 03/087737 | 10/2003 |
| WO | WO 04/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/148172 | 12/2008 |
| WO | WO 2009/137524 | 11/2009 |
| WO | WO 2009/155593 | 12/2009 |
| WO | WO 2010/078168 | 7/2010 |

(56) References Cited

FOREIGN PATENT DOCUMENTS

| WO | WO 2011/047207 | 4/2011 |
|---|---|---|
| WO | WO 2011/047209 | 4/2011 |
| WO | WO2011/047211 | 4/2011 |
| WO | WO 2011/047213 | 4/2011 |
| WO | WO 2011/047216 | 4/2011 |
| WO | WO 2013/056141 | 4/2013 |

OTHER PUBLICATIONS

U.S. Appl. No. 12/905,530, filed Oct. 15, 2010, Al-Ali et al.
U.S. Appl. No. 12/905,489, filed Oct. 15, 2010, Weber et al.
U.S. Appl. No. 12/905,449, filed Oct. 15, 2010, Al-Ali et al.
U.S. Appl. No. 12/905,384, filed Oct. 15, 2010, Al-Ali et al.
U.S. Appl. No. 13/554,908, filed Jul. 20, 2012, Telfort et al.
U.S. Appl. No. 13/152,259, filed Jun. 2, 2011, Kiani.
Analog Devices, 12-Bit Serial Input Multiplying D/A Converter, Product Data Sheet, 2000.
Avago Technologies, "HCNR200 and HCNR201, High-Linearity Analog Optocouplers," Data Sheet, Avago Technologies, Nov. 18, 2008.
Images showing tear down of a Measurement Specialties' stethoscope, Images taken on Sep. 7, 2007, in 38 pages.
Sierra et al., Monitoring Respiratory Rate Based on Tracheal Sounds. First Experiences, Proceedings of the 26th Annual Int'l Conf. of the IEEE EMBS (Sep. 2004), 317-320.
WelchAllyn OEM Technologies, ECG ASIC, ECG 3-lead, 5-lead, 12-lead and RESP Signal Processing, ECG ASIC Part No. 000.91163 (2001).
Eldor et al., "A device for monitoring ventilation during anaesthesia; the paratracheal audible respiratory monitor", Canadian Journal of Anaesthesia, 1990, vol. 9, No. 1, p. 95-98.
US 8,740,816, 06/03/2014, Telfort et al. (withdrawn).
International Search Report & Written Opinion, PCT Application PCT/US2010/052758, Feb. 10, 2011; 12 pages.
International Search Report & Written Opinion, PCT Application PCT/US2010/058981, Feb. 17, 2011; 11 pages.
International Search Report and Written Opinion for PCT/US2009/042902, mailed Dec. 8, 2009.
International Search Report, PCT Application PCT/CA2003/000536, Dec. 11, 2003; 2 pages.
EP Office Action dated May 18, 2011 in application No. 03711767.8.
Japanese Office Action re Application No. 2007-506626, dated Mar. 1, 2011.
PCT Invitation to Pay Fees and Initial Search Report in PCT/US2010/052756, dated Oct. 5, 2011.
International Search Report & Written Opinion for PCT/US2010/052756, mailed Feb. 6, 2012; 17 pages.
PCT Invitation to Pay Fees and Initial Search Report in PCT/US2009/069287, dated Apr. 21, 2010.
International Search Report and Written Opinion issued in PCT Application No. PCT/US2009/069287, Jun. 30, 2010.
Office Action in Japanese Application No. 2011-544508 mailed Apr. 30, 2014.
EP Office Action dated Mar. 5, 2013 in application No. 10779086.7.
PCT Invitation to Pay Fees and Initial Search Report in PCT/US2010/052754, dated Mar. 15, 2011.
International Search Report and Written Opinion in PCT/US2010/052754 mailed Jul. 27, 2011.
International Preliminary Report on Patentability (IPRP) in PCT/US2010/052754, dated Apr. 26, 2012.
International Search Report and Written Opinion in PCTUS2010052760 mailed Mar. 8, 2011 in 11 pages.
International Search Report and Written Opinion in PCT/US2010/052763, mailed May 13, 2011.
International Preliminary Report on Patentability in PCT/US2010/052763 dated Apr. 17, 2012 in 9 pages.
International Search Report and Written Opinion dated Dec. 21, 2012 for PCT Application No. PCT/US2012/060084.
International Preliminary Report on Patentability dated Apr. 15, 2014 for PCT Application No. PCT/US2012/060084.
European Search Report for Application No. 13185148.7 dated Dec. 6, 2013.

\* cited by examiner

ACOUSTIC RESPIRATORY MONITORING SENSOR WITH PROBE-OFF DETECTION

CROSS-REFERENCE TO RELATED APPLICATIONS

This application claims the benefit of priority from U.S. Provisional Application No. 61/510,926, filed Jul. 22, 2011, which is incorporated in its entirety by reference herein.

BACKGROUND

Certain existing patient monitoring systems include biological sound sensors that capture patient bodily sounds (e.g., heart, breathing, digestive system sounds, etc.) and physiological monitors which process the captured sounds to determine physiological parameters. Such systems generally rely on a robust connection between the sensor and the patient to reliably detect and process the targeted bodily sounds. As such, a faulty or unstable connection between the sensor and the patient (e.g., a "probe-off" condition) can lead to a number of problems, particularly where the patient monitor or medical personnel are not made aware of the issue.

When the physiological monitor is not aware of a faulty connection between the sensor and patient, the monitor may misinterpret readings detected by the sensor. For example, the monitor may indicate false alarm conditions. In one instance, where the system is configured to detect patient breathing sounds and determine a corresponding respiratory rate, the monitor may falsely determine that the patient is not breathing, instead of merely indicating that the sensor has detached from the patient's skin. The system may additionally detect significant amounts of environmental noise due to a probe-off condition, and then improperly present the detected noise as physiological signal. Moreover, medical personnel may similarly misinterpret results presented by the monitor when the personnel are not aware of a faulty connection, possibly leading to misdiagnoses or other issues.

For these and other reasons, there is a need for an acoustic physiological sensor having reliable and straightforward probe-off detection capability.

SUMMARY

Embodiments of systems including an acoustic sensor and/or physiological monitor described herein are configured to provide accurate and robust measurement of bodily sounds under a variety of conditions, such as in noisy environments or in situations in which stress, strain, or movement can be imparted onto the sensor with respect to a patient. For example, in certain embodiments the sensor and/or monitor include probe-off detection capability that indicates the connection quality between the sensor and patient.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught or suggested herein without necessarily achieving others.

An acoustic sensor is provided that is configured to noninvasively detect acoustic vibrations associated with a medical patient. The acoustic vibrations are indicative of one or more physiological parameters of the medical patient. According to various aspects, the sensor can include a sensor support and at least one sound sensing membrane supported by the sensor support and configured to detect acoustic vibrations associated with a medical patient. The sensing membrane may also be configured to produce a membrane signal corresponding to the acoustic vibrations when the acoustic sensor is attached to the medical patient. The sensor can also include a probe-off assembly supported by the sensor support, where the probe off-assembly is configured to produce a probe-off signal responsive to attachment of the acoustic sensor to the medical patient and detachment of the acoustic sensor from the medical patient.

The probe-off signal may indicate a sensor connected condition when the sensor is attached to the patient and a sensor not connected condition when the sensor is not attached to the patient. The probe-off signal can also be indicative of the integrity of a connection between the acoustic sensor and the patient. In certain instances, the probe-off assembly has a switch configured to actuate in response to attachment of the sensor to the patient. The actuation of the switch can result in a corresponding change in the output of the probe-off assembly that is indicative of a probe-off condition. In certain embodiments, the probe-off assembly is positioned to actuate in response to a force that is in the direction of the patient's skin when the sensor is attached to the patient.

According to some aspects, a mechanically active portion of the at least one sound sensing membrane which moves in response to the acoustic vibrations is between the patient's skin and the probe-off assembly when the sensor is attached to the patient. Moreover, in some cases, at least a portion of the sensor support is between a patient contact surface of the sensor and the probe-off assembly.

The acoustic sensor may further include at least one attachment member supported by the sensor support and configured to move from a first position when not attached to the patient to a second position when attached to the medical patient. Moreover, the probe-off signal is responsive to the movement of the attachment member between the first position and the second position to indicate a change in the integrity of the connection between the acoustic sensor and the medical patient. In such cases, the probe-off assembly can further include a switch supported by the sensor support. Movement of the at least one attachment member from the first position to the second position may actuate the switch. The sensor can include a substantially rigid shell supported by the sensor support, where at least a portion of the shell is positioned over the switch.

The attachment member can include a resilient, elongate member, and in some cases the attachment member extends across the sensor support and beyond opposing sides of the sensor support. The attachment member may further include an adhesive adapted to secure the attachment member to the medical patient's skin.

The sensor may further include a resilient portion supported by the sensor support and arranged to bias the attachment member in the first position when the sensor is in an unattached state. The resilient portion can form a part of a casing stretched around and encasing at least a portion of the sensor support.

In some embodiments, a physiological monitor in communication with the acoustic sensor is responsive to the probe-off signal to determine either a sensor connected condition or a sensor not connected condition. The acoustic sensor can include an output that is responsive to both the membrane signal and to the probe-off signal. A sensing circuit responsive to the output may produce a sensor signal which is both indicative of the integrity of the connection between the acoustic sensor and the patient and which, when the acoustic sensor is attached to the medical patient, corresponds to the acoustic vibrations detected by the sensing membrane. In some cases, the sensing circuit is located on a cable positioned between the acoustic sensor and the physiological monitor. The cable may be configured to communicatively couple the acoustic sensor and the physiological monitor.

A method is also provided for determining a connection state between a non-invasive acoustic sensor and a medical patient. The method can include outputting from a non-invasive acoustic sensor, a signal indicating that the acoustic sensor is in an unattached state in response to at least one attachment member of the sensor being in a first position, the sensor configured to detect acoustic vibrations indicative of one or more physiological parameters of the medical patient. The method can further include outputting a signal from the sensor indicating that the acoustic sensor is in an attached state in response to the at least one attachment member moving from the first position to a second position. In some embodiments, the method includes outputting a signal from the sensor indicative of the one or more physiological parameters when the sensor is in the attached state.

According to additional aspects, a patient monitoring system is also provided that is configured to communicate with a non-invasive acoustic sensor. The monitoring system can include a communication port configured to receive at least one signal responsive to at least one output of a non-invasive acoustic sensor. The acoustic sensor may be configured to detect acoustic vibrations associated with a medical patient and include a probe-off assembly responsive to attachment and detachment of the acoustic sensor to and from a surface. The at least one output of the acoustic sensor can be responsive to the probe-off assembly and to the acoustic vibrations. The monitoring system can further include a processor communicatively coupled to the communication port and configured to, in response to the signal, determine whether the sensor is in an unattached state.

BRIEF DESCRIPTION OF THE DRAWINGS

Throughout the drawings, reference numbers can be reused to indicate correspondence between referenced elements. The drawings are provided to illustrate embodiments of the inventions described herein and not to limit the scope thereof.

DETAILED DESCRIPTION

Figure 1A:
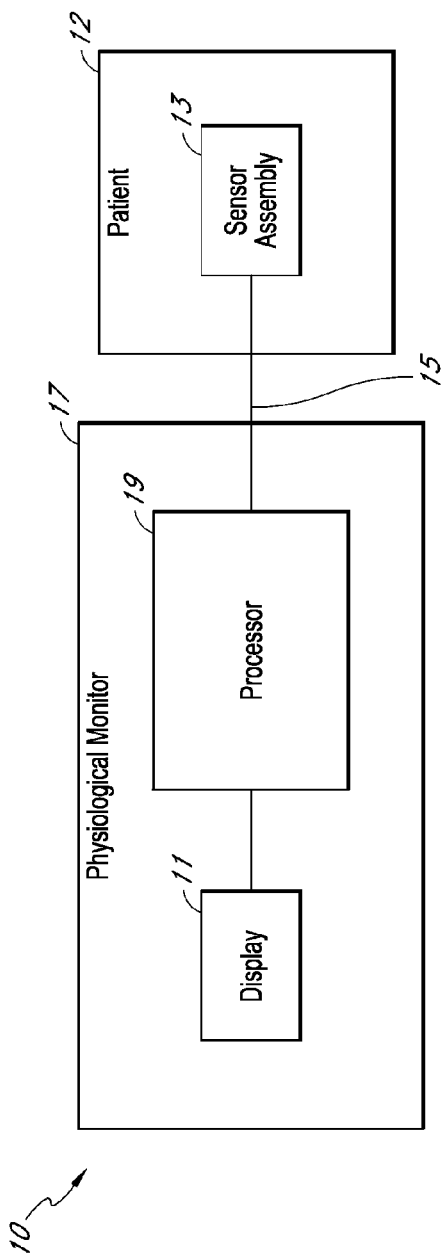
FIGS. 1A-B are block diagrams illustrating physiological monitoring systems in accordance with embodiments of the disclosure.

Various embodiments will be described hereinafter with reference to the accompanying drawings. These embodiments are illustrated and described by example only, and are not intended to be limiting.

Probe-Off Overview

Embodiments described herein include sensors and sensor systems having probe-off detection componentry. For example, sensors and physiological monitors described herein include dedicated mechanical components and/or circuitry capable of providing an indication of the integrity of the connection between the sensor and the patient.

Where an acoustic sensor does not incorporate separate probe-off functionality, physiological monitors can in some cases nonetheless be configured to process signals received from the sensor to determine the connection state. However, in such cases, it can be difficult to provide a reliable determination. For example, the sensor may detect significant environmental noise when it is not connected to the patient. The environmental noise may closely resemble target bodily sounds, or may otherwise not be sufficiently different from the bodily sounds for the monitor to determine the connection state to a desirable degree of certainty. Thus, from physiological signals (such as acoustic readings) alone, it can be difficult to determine a connection state. Moreover, to the extent that monitors can determine the connection state in such cases, monitors may employ relatively complex signal processing algorithms to make the determination.

To address these and other potential issues, certain sensors described herein advantageously include dedicated componentry to provide reliable and cost-effective probe-off detection. As a few examples, the sensor may provide the monitor with a signal usable to determine the connection state, the sensor may directly provide the monitor with an indication of the connection state, or the sensor may provide an indication of the connection state directly to medical personnel.

Moreover, some of the probe-off techniques described herein advantageously incorporate or cooperate with portions of the sensor that also serve other, non-probe functions. For example, sensors can include attachment arms or other mechanisms that have adhesive surfaces, allowing a user to affix the sensor to the patient. The state of the attachment element is naturally indicative of whether or not the sensor is attached to the patient. Thus, utilizing the attachment mechanism with probe-off detection helps provide robust and straightforward probe-off capability. In some cases, the probe-off componentry responds to actuation of such attachment mechanisms. For example, movement of the attachment elements to affix the sensor to the patient may trigger a probe-off detection switch. The switch in turn outputs a signal usable by the monitor to determine whether or not the sensor is connected to the patient. In some cases, the resilient nature of an elastomeric casing is used in the probe-off detection. For example, the casing or a portion thereof cooperates with the probe-off componentry (e.g., a switch) and/or sensor attachment elements to provide probe-off reliable detection. Such techniques are described in greater detail below with respect to specific embodiments.

Moreover, according to certain aspects, the probe-off componentry can be positioned on the sensor to provide improved accuracy and reliability in probe-off detection and/or physiological measurement. In one case, the sensor includes an active portion, which includes a piezoelectric membrane and a patient contact surface. The active portion is generally designed to interact with the patient and move in response to bodily sounds. A switch of a probe-off assembly may be advantageously spaced from the active portion of the sensor, thereby preventing the switch from interfering with the operation of the active portion. Such an arrangement can also prevent the switch from becoming soiled or otherwise damaged, from interaction with the patient's skin for example.

The probe-off techniques described herein can be used in a variety of ways to improve patient monitoring. For example, the patient monitor can provide medical personnel with an indication of the quality of the attachment state of the sensor, such as "sensor connected," "sensor disconnected," "sensor improperly connected," an indication (e.g., a percentage or other alphanumeric indication) as to the degree of the connection quality, or some other indication of the connection quality. Additionally, by alerting the monitor and/or medical personnel to probe-off conditions, the probe-off componentry described herein reduces the risk that targeted physiological sounds will go un-monitored for extended periods of time.

Moreover, the sensor, monitor, and/or user may use the indication of the attachment state to avoid false positive (e.g., alarm) conditions. For example, where a system is monitoring patient breathing sounds and the sensor becomes disconnected, the monitor can use the probe-off functionality to avoid reporting a false alarm to medical personnel that the patient is not breathing. Instead, the monitor can report the probe-off and/or false alarm condition to personnel, who will in turn fix the faulty connection. A wide variety of other uses or combinations of the uses described herein are possible. For example, in one embodiment, the sensor or monitor stops detecting and/or reporting sound information when the sensor is not properly attached to a patient. Moreover, by alerting medical personnel to probe-off conditions, the probe-off module reduces the risk that the targeted physiological sounds will go un-monitored for extended periods of time.

While described with respect to acoustic sensors configured to detect physiological sounds of a patient, many of the techniques described herein are compatible with other types of patient sensors (e.g., pulse oximetry sensors, capnography sensors, and the like). Additionally, the term "probe-off" is not to be interpreted as limiting. Rather, the meaning of the term "probe-off" as used herein will be appreciated in view of its usage throughout the disclosure, and is often used, for example, to refer generally to the components and processes capable of determining an integrity of the connection between the sensor and the patient.

A contextual system overview is provided below with respect to FIGS. 1A-1C, and further embodiments incorporating probe-off functionality are then shown and described herein with respect to FIGS. 2-7B.

System Overview

In various embodiments, an acoustic sensor configured to operate with a physiological monitoring system includes an acoustic signal processing system that measures and/or determines any of a variety of physiological parameters of a medical patient. For example, in an embodiment, the physiological monitoring system includes an acoustic monitor. The acoustic monitor may be an acoustic respiratory monitor which can determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases the acoustic signal processing system monitors other physiological sounds, such as heart rate to help with probe off detection, heart sounds (S1, S2, S3, S4, and murmurs), and change in heart sounds such as normal to murmur or split heart sounds indicating fluid overload. Moreover, the acoustic signal processing system may (1) use a second probe over the chest for additional heart sound detection; (2) keep the user inputs to a minimum (example, height); and/or (3) use a Health Level 7 (HL7) interface to automatically input patient demography.

In certain embodiments, the physiological monitoring system includes an electrocardiograph (ECG or EKG) that measures and/or determines electrical signals generated by the cardiac system of a patient. The ECG includes one or more sensors for measuring the electrical signals. In some embodiments, the electrical signals are obtained using the same sensors used to obtain acoustic signals.

In still other embodiments, the physiological monitoring system includes one or more additional sensors used to determine other desired physiological parameters. For example, in some embodiments, a photoplethysmograph sensor determines the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In other embodiments, a capnograph determines the carbon dioxide content in inspired and expired air from a patient. In other embodiments, other sensors determine blood pressure, pressure sensors, flow rate, air flow, and fluid flow (first derivative of pressure). Other sensors may include a pneumotachometer for measuring air flow and a respiratory effort belt. In certain embodiments, these sensors are combined in a single processing system which processes signal output from the sensors on a single multi-function circuit board.

Figure 1B:
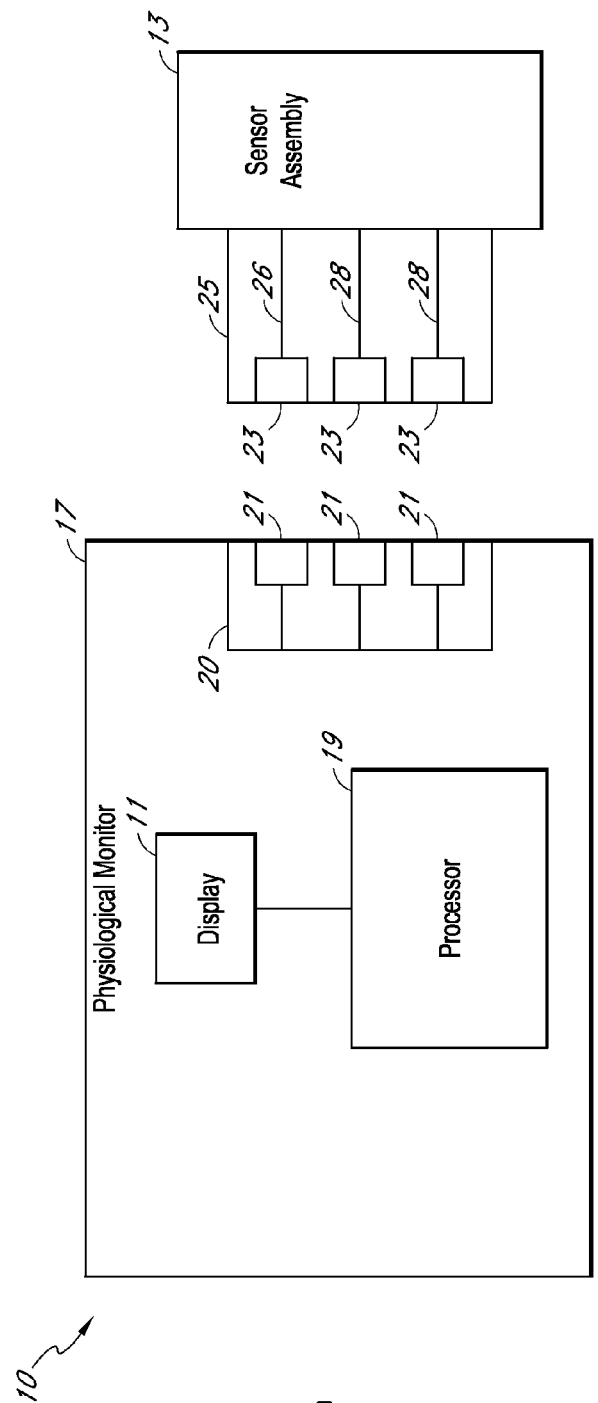
Figure 1C:
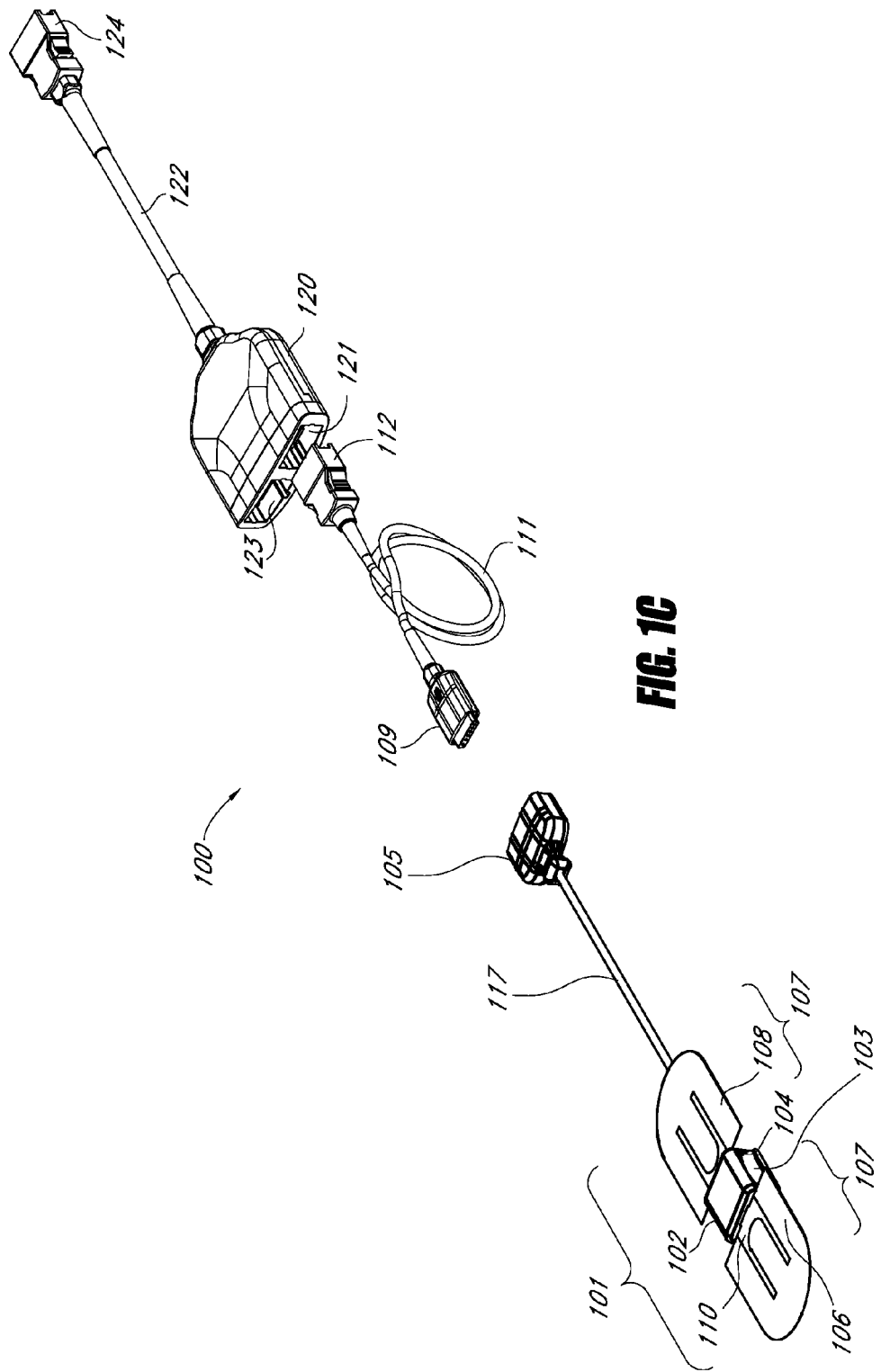
FIG. 1C is a top perspective view illustrating portions of a sensor system in accordance with an embodiment of the disclosure.

Referring to the drawings, FIGS. 1A through 1C illustrate example patient monitoring systems, sensors, and cables that can be used to provide acoustic physiological monitoring of a patient, such as respiratory monitoring, with probe-off detection. FIGS. 5A-5F, 6A-6G, and 7A-7B illustrate additional embodiments of sensors and systems incorporating probe-off detection.

FIG. 1A shows an embodiment of a physiological monitoring system 10. In the physiological monitoring system 10, a medical patient 12 is monitored using one or more sensors 13, each of which transmits a signal over a cable 15 or other communication link or medium to a physiological monitor 17. The physiological monitor 17 includes a processor 19 and, optionally, a display 11. The one or more sensors 13 include sensing elements such as, for example, acoustic piezoelectric devices, electrical ECG leads, pulse oximetry sensors, or the like. The sensors 13 can generate respective signals by measuring a physiological parameter of the patient 12. The signals are then processed by one or more processors 19. The one or more processors 19 then communicate the processed signal to the display 11 if a display 11 is provided. In an embodiment, the display 11 is incorporated in the physiological monitor 17. In another embodiment, the display 11 is separate from the physiological monitor 17. The monitoring system 10 is a portable monitoring system in one configuration. In another instance, the monitoring system 10 is a pod, without a display, and is adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, and the like. In each of the foregoing embodiments, additional sensors of different types are also optionally included. Other combinations of numbers and types of sensors are also suitable for use with the physiological monitoring system 10.

In some embodiments of the system shown in FIG. 1A, all of the hardware used to receive and process signals from the sensors are housed within the same housing. In other embodiments, some of the hardware used to receive and process signals is housed within a separate housing. In addition, the physiological monitor 17 of certain embodiments includes hardware, software, or both hardware and software, whether in one housing or multiple housings, used to receive and process the signals transmitted by the sensors 13.

As shown in FIG. 1B, the acoustic sensor 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the sensor 13 to the physiological monitor 17. For multiple sensors, one or more additional cables 115 can be provided.

In some embodiments, the ground signal is an earth ground, but in other embodiments, the ground signal is a patient ground, sometimes referred to as a patient reference, a patient reference signal, a return, or a patient return. In some embodiments, the cable 25 carries two conductors within an electrical shielding layer, and the shielding layer acts as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly.

FIG. 1C illustrates an embodiment of a sensor system 100 including a sensor 101 suitable for use with any of the physiological monitors shown in FIGS. 1A and 1B. The sensor system 100 includes a sensor 101, a sensor cable 117, and a connector 105 attached to the sensor cable 117. The sensor 101 includes a shell 102, an acoustic coupler, 103 and a frame 104, which may also be referred to as a sensor support, configured to house certain componentry of the sensor 101, and an attachment portion 107 positioned on the sensor 101 and configured to attach the sensor 101 to the patient.

The sensor 101 can be removably attached to an instrument cable 111 via an instrument cable connector 109. The instrument cable 111 can be attached to a cable hub 120, which includes a port 121 for receiving a connector 112 of the instrument cable 111 and a second port 123 for receiving another cable. In certain embodiments, the second port 123 can receive a cable connected to a pulse oximetry or other sensor. In addition, the cable hub 120 could include additional ports in other embodiments for receiving additional cables.

The hub includes a cable 122 which terminates in a connector 124 adapted to connect to a physiological monitor (not shown). In another embodiment, no hub is provided and the acoustic sensor 101 is connected directly to the monitor, via an instrument cable 111 or directly by the sensor cable 117, for example. Examples of compatible hubs are described in U.S. patent application Ser. No. 12/904,775, which is incorporated by reference in its entirety herein.

The component or group of components between the sensor 101 and the monitor in any particular embodiment may be referred to generally as a cabling apparatus. For example, where one or more of the following components are included, such components or combinations thereof may be referred to as a cabling apparatus: the sensor cable 117, the connector 105, the cable connector 109, the instrument cable 111, the hub 120, the cable 122, and/or the connector 124. It should be noted that one or more of these components may not be included, and that one or more other components may be included between the sensor 101 and the monitor, forming the cabling apparatus.

In an embodiment, the acoustic sensor 101 includes one or more sensing elements (not shown), such as, for example, a piezoelectric device or other acoustic sensing device. Where a piezoelectric membrane is used, a thin layer of conductive metal can be deposited on each side of the film as electrode coatings, forming electrical poles. The opposing surfaces or poles may be referred to as an anode and cathode, respectively. Each sensing element can be configured to mechanically deform in response to sounds emanating from the patient (or other signal source) and generate a corresponding voltage potential across the electrical poles of the sensing element.

The shell 102 according to certain embodiments houses a frame (not shown) or other support structure configured to support various components of the sensor 101. The one or more sensing elements can be generally wrapped in tension around the frame. For example, the sensing elements can be positioned across an acoustic cavity disposed on the bottom surface of the frame. Thus, the sensing elements according to some embodiments are free to respond to acoustic waves incident upon them, resulting in corresponding induced voltages across the poles of the sensing elements.

Additionally, the shell 102 can include an acoustic coupler (not shown), which advantageously improves the coupling between the source of the signal to be measured by the sensor (e.g., the patient's body) and the sensing element. The acoustic coupler 102 of one embodiment includes a bump positioned to apply pressure to the sensing element so as to bias the sensing element in tension. For example, the bump can be positioned against the portion of the sensing element that is stretched across the cavity of the frame. In one embodiment, the acoustic coupler further includes a protrusion (not shown) on the upper portion of the inner lining, which exerts pressure on the backbone 110 (discussed below) and other internal components of the sensor 101.

The attachment portion 107 helps secure the sensor assembly 101 to the patient. The illustrated attachment portion 107 includes first and second attachment arms 106, 108. The attachment arms can be made of any number of materials, such as plastic, metal or fiber. Furthermore, the attachment arms can be integrated with the backbone (discussed below). The underside of the attachment arms 106, 108 include patient adhesive (e.g., in some embodiments, tape, glue, a suction device, etc.), which can be used to secure the sensor 101 to a patient's skin. The example attachment portion 107 further includes a resilient backbone member 110 which extends into and forms a portion of the attachment arms 106, 108. The backbone 110 can be placed above or below the attachment arms 106, 108, or can be placed between an upper portion and a lower portion of the attachment arms 106, 108. Furthermore, the backbone can be constructed of any number of resilient materials, such as plastic, metal, fiber, combinations thereof, or the like.

As the attachment arms 106, 108 are brought down into contact with the patient's skin on either side of the sensor 102, the adhesive affixes to the patient. Moreover, the resiliency of the backbone 110 causes the sensor 101 to be beneficially biased in tension against the patient's skin and/or reduces stress on the connection between the patient adhesive and the skin. Further examples of compatible attachment portions, associated functionality and advantages are described in U.S. application Ser. No. 12/643,939 (the '939 application) previously incorporated by reference. For example, embodiments of attachment portions are shown in and described with respect to FIGS. 2B, 2C, 9A-9D and 10 of the '939 application, and are explicitly incorporated by reference herein.

Moreover, as will be described in greater detail, the attachment portion 107 can also advantageously work together with other sensor componentry to provide an indication to the monitor or to the user as to the attachment state of the sensor.

The acoustic sensor 101 can further include circuitry for detecting and transmitting information related to biological sounds to the physiological monitor. These biological sounds can include heart, breathing, and/or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein (the '883 application). In other embodiments, the acoustic sensor 101 is a biological sound sensor such as those described in U.S. Pat. No. 6,661,161 or U.S. patent application Ser. No. 12/643,939, filed on Dec. 21, 2009 (the '939 application), both of which are incorporated by reference herein in their entirety. Other embodiments include other suitable acoustic sensors. For example, in certain embodiments, compatible acoustic sensors can be configured to provide a variety of auscultation functions, including live and/or recorded audio output (e.g., continuous audio output) for listening to patient bodily or speech sounds. Examples of such sensors and sensors capable of providing other compatible functionality can be found in U.S. patent application Ser. No. 12/905,036 entitled PHYSIOLOGICAL ACOUSTIC MONITORING SYSTEM, filed on Oct. 14, 2010, previously incorporated by reference herein in its entirety.

While an example sensor system 100 has been provided, embodiments described herein are compatible with a variety of sensors and associated components.

Example Systems and Sensors Incorporating Probe-Off Functionality

Figure 2:
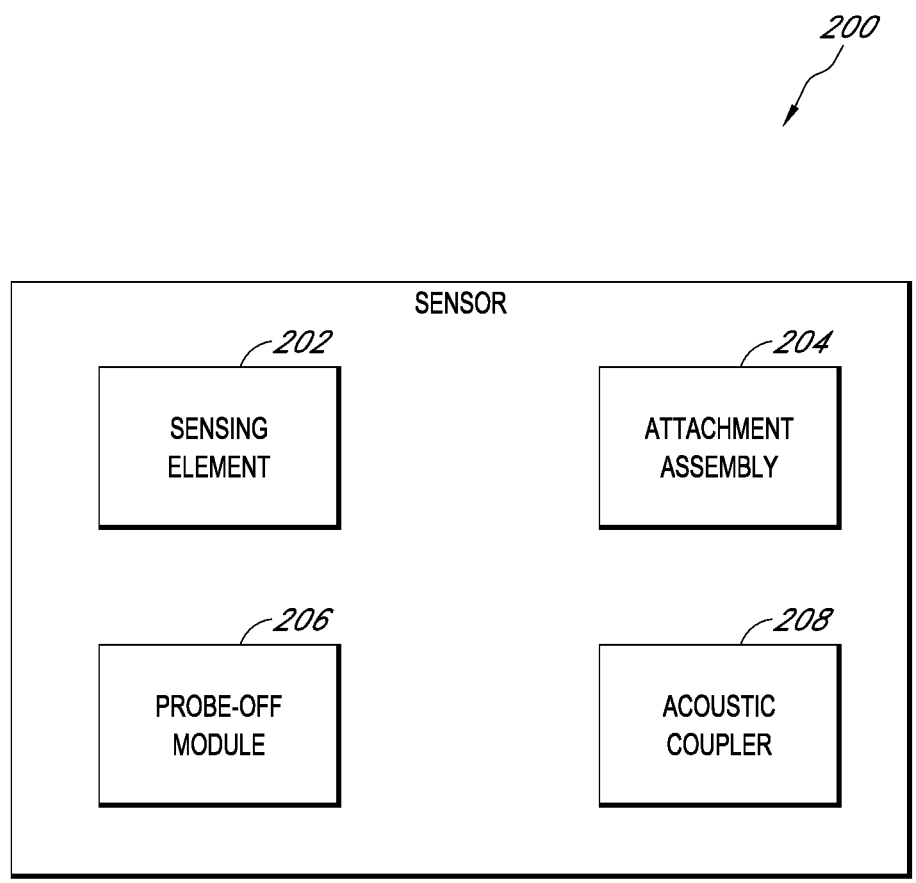
FIG. 2 is a block diagram illustrating a sensor incorporating probe-off componentry in accordance with an embodiment of the disclosure.

FIG. 2 is a block diagram illustrating an acoustic sensor assembly 200 incorporating probe-off componentry, also referred to as a probe-off assembly, in accordance with an embodiment of the disclosure. The sensor assembly 200 includes a sensing element 202, an attachment assembly 204, a probe-off module 206 and an acoustic coupler 208. The sensing element 202 of the example sensor 200 detects patient bodily sounds, and can be any of the acoustic sensing elements described herein, or some other type of sensing element.

The attachment assembly 204 generally attaches the sensor assembly to the patient, and can include an adhesive, such as glue, tape, or the like. For example, the attachment assembly 204 can include the attachment arms 106, 108 described above with respect to FIG. 1C, or may be one of the attachment assemblies described below with respect to FIGS. 5A-5B and 6A-8B.

The probe-off module 206 generally provides an indication as to the quality of the connection between the sensor and the patient, such as whether or not the sensor 200 is properly attached to the patient. Compatible probe-off module 206 will be described in greater detail below. For example, as described with reference to FIGS. 4, 5A-5B, and 6A-8B, in certain embodiments, the probe-off module 206 includes a switch (e.g., an electromechanical switch) that actuates in response to attachment and disconnection of the sensor from the patient.

Moreover, in various embodiments, the probe-off module 206 can be implemented using a variety of technologies and techniques, such as passive, active, electrical, electromagnetic, mechanical, or chemical technologies. For example, the probe-off module 206 can be implemented using skin resistance, capacitive touch, heat, IR light from the patient, ambient visible light, reflected or refracted light from the patient, frequency detection from a patient, magnetic field detection, EKG, ECG, magnetic switches, acoustic cavities, acoustic impedance, mechanical impedance, physical pushbuttons, physical switches, chemical reaction, combinations of the same and the like. In one embodiment, a IR (or heat) sensor detects the proximity of the patient to the sensor. As the sensor nears the patient and is attached to the patient, the IR sensor readings change. Once a threshold heat level is reached, a switch is activated. The threshold level can be set based on expected heat levels of the patient.

In an alternative embodiment, a chemical reaction between the patient's skin and the sensor causes the sensor to begin outputting data. For example, the patient's skin or oil from the patient's skin can be used to create a chemical reaction that activates the switch. In yet another embodiment, the probe-off module 206 can include an ohmmeter to detect the amount of resistance (or impedance) between two conductive points on the sensor. The two conductive points can be located on the portion of the sensor that comes in contact with the patient's skin. When the resistance between the two points meets a threshold level, the switch is activated. The threshold level can be set based on skin conductance or resistance. Similarly, a capacitive sensor disposed, for example, on the sensor 101 or positioned elsewhere on the patient can be used to detect when the patient's skin comes in contact with the sensor. Based on the readings, the switch can activate.

For example, in one embodiment, a conductive element or material is disposed on one or more of the following locations of the sensor 101 to thereby act as one or both of the two conductive points for determining resistance: one or both of the attachment arms 106/108, the backbone 110, the shell 102, or the frame 104. In one embodiment, the conductive element is a conductive film. A conductive film can be disposed on the skin-facing surface of the attachment arms 106, 108, for example. One material that may be used for the conductive film is silver chloride, although other materials may also be used. Instead of a conductive film, the conductive element may be a metal material. For instance, the backbone 110 can be made of conductive material such as copper or aluminum. One or both of the two conductive points on the sensor can also act as an ECG sensor. In another embodiment, one conductive point or element is disposed on the sensor, and a second conductive element is disposed elsewhere on the body, such as in a separate ECG lead.

To improve conductivity between the conductive element or elements and the patient's skin, a gel material can be applied on the patient's skin prior to applying the conductive element to the patient's skin. In one embodiment, the sensor can include a gel layer on top of the conductive element or elements disposed on the sensor. The gel layer, if disposed on the shell 102 or frame 104, can also act as an acoustic medium that improves acoustic coupling between the sensor and the patient.

In yet another embodiment, a light meter is used to detect when the sensor is connected to the patient. The light meter can be located on the side of the sensor closest to the patient. When the sensor is in contact with the patient, light is obstructed from reaching the light meter. Based on a threshold light meter level, the switch is activated. Similarly, the light meter can measure reflected or refracted light from the patient to determine if the sensor is attached to the patient. An EKG or ECG device can also be used to detect whether the sensor is attached to the patient. Once the EKG or ECG device detects electrical activity from the patient's heart, the switch can be activated. Alternatively, a bioelectric sensor can attached to the sensor and used to detect electric potential or electromagnetic fields from the patient or the patient's skin. When the electric potential or electromagnetic field measurements reach a threshold level, the switch is activated. Furthermore, the sensor can be configured to activate when sounds within a particular frequency range and/or magnitude are observed by the sensor. In addition, a push button switch can be provided that is activated by a medical caregiver when the sensor is attached. Other methods can be used to implement the switch without departing from the spirit and scope of the description.

The acoustic coupler 208 generally improves the coupling between the source of the signal and the sensing element 202, and may comprise an elastomeric casing or any of the couplers described herein (e.g., with respect to FIGS. 5A-5F).

Figure 3:
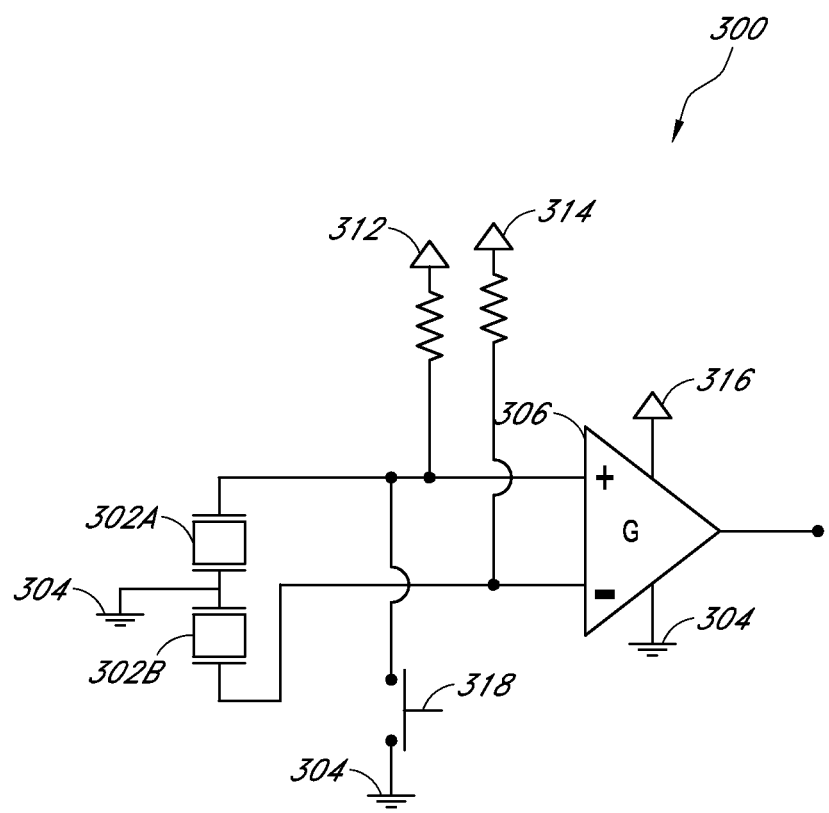
FIG. 3 is a schematic illustration of an embodiment of acoustic physiological sensing circuitry with a probe-off detection circuit.

FIG. 3 is a schematic illustration of an embodiment of an acoustic sensing circuit 300. Certain portions of the illustrated circuit 300 form a part of an acoustic sensor which incorporates probe-off componentry. The example sensor has two sensing elements 302A, 302B (e.g., piezoelectric membranes) connected in the manner described below to provide a physiological signal. For example, certain portions of the sensing circuitry 300 may be included in any of the sensors described herein. In some embodiments, the sensing elements are arranged in a stacked configuration on a frame, as shown in and described herein with respect to FIGS. 5A-5F and 6A-6B. As will be described in further detail, certain other portions of the example sensing circuitry 300 may not be located on the sensor itself, but may instead be located on one or more other components of the physiological sensing system.

In addition, the example sensing circuit 300 includes probe-off circuitry configured to provide an indication as to the quality of the connection between the patient and the sensor. For example, the sensing circuit 300 or portions thereof may form a part of any of the probe-off componentry described herein.

The example sensing circuit 300 includes piezoelectric membranes 302A, 302B, a sensing device 306, power sources connections 312, 314, 316, and a switch 318. The output of the piezoelectric membrane 302A is connected to a positive terminal of the sensing device 306 and the output of the piezoelectric membrane 302B is connected to a negative, or inverting, terminal of the sensing device 306. The membranes 302A, 302B are also connected to a common ground 304. The sensing device 306 can include additional components, such as feedback loops, feedback resistors, capacitors, and the like, which are not shown for the purposes of illustration. The piezoelectric membranes 302A, 302B generally detect mechanical vibrations (e.g., from patient physiological sounds) and generate corresponding electrical waveforms.

Referring to FIGS. 1 and 3, in the illustrated embodiments, the piezoelectric membranes 302A, 302B and the switch 318 are physically located on the sensor 101 itself, while the sensing device 306 is physically located on the instrument cable 111. For example, in one embodiment, the sensing device 306 is located on the sensor connector 109 of the instrument cable 111 which connects to the sensor cable 117. In another embodiment, the sensing device is located on the connector 112 of the instrument cable which connects to the hub 120. In other cases, the arrangement of the various components of the sensing circuitry can vary. For example, in various configurations, the sensing device 306 or a portion thereof may be positioned on the sensor 101 itself, on the connector 105 of the sensor cable 105, on the hub 120, on the monitor connector 124, the physiological monitor itself, or on any of the cables 117, 111, 122.

Moreover, the membranes 302A, 302B are configured such that the waveforms generated by the piezoelectric membranes 302A, 302B are of opposite polarity, or 180° or approximately 180° out of phase, providing improved signal-to-noise ratio as compared to embodiments including a single membrane. For example, the sensing device 306 is arranged as a differential amplifier and generally constructively combines the waveforms from the two piezoelectric membranes to create an output signal indicative of the sensed physiological sounds. In one example embodiment, the sensing device 306 is arranged as a differential amplifier, the power source connections 312, 314 provide 2.5V DC reference voltages, and the power source connection 316 is connected to a 5V DC power source. In such a configuration, during normal operation, when the switch 318 is open, the sensing device 306 provides an AC output signal representative of sounds detected by the sensing elements 302A, 302B, which swings around the 2.5V DC reference value between 0V and 5V. In other embodiments, the sensor 300 includes a single membrane, or includes more than two membranes.

The sensing device 306 can include one or more operational amplifiers. U.S. application Ser. No. 12/904,931 (the '931 application) includes further examples of sensing circuits that are compatible with the embodiments described herein (e.g., as shown in and described with respect to FIGS. 3A and 3B of the '931 application), and each of which are explicitly incorporated in their entirety by reference herein.

The circuit 300 can include componentry used in the probe-off determination, providing an indication as to the quality of the connection between the patient and the sensor. For example, the sensor may be configured such that the switch 318 closes when the sensor is not properly attached to the patient. When closed, the switch 318 is configured to electrically couple the positive terminal of the sensing device 306 to ground 304 (e.g., 0V). In certain configurations, such as where the sensing device 306 comprises a differential amplifier, the 0V input on the positive terminal will force the output of the sensing device 306 to 0V or substantially 0V. Thus, the output characteristic (e.g., frequency profile) of the sensing device 306 is advantageously significantly altered when the switch 318 is closed (probe-off condition) as compared to when the switch 318 is open (probe-on condition). In turn, the resulting change in the output characteristic can be used to determine the connection state of the sensor in a reliable and straightforward manner. For example, the monitor may receive and process the output of the sensing device 306 or a version thereof to determine the sensor connection state. Thus, the use of the switch 318 to indicate whether the sensor is in an attached state can significantly improve the robustness of the probe-off detection, reducing possible instances where the monitor and/or medical personnel misinterpret sensor readings. Furthermore, the use of the switch 318 can allow care providers to be able to place greater confidence in error or warning signals provided by the monitor. While one terminal of the switch 318 is tied to ground 304 (e.g., 0V) in the illustrated embodiment, in other configurations that terminal is tied to some other potential. For instance, the switch 318 may be connected to a node having some DC bias (e.g., 0.5V, 1V, 1.5V, 2V, or any other appropriate value). In such cases, and in a manner similar to the embodiment where 0V is used, the output characteristic (e.g., frequency profile) of the sensing device 306 will be significantly altered, providing a robust indication as to whether the sensor is in an attached state. In some embodiments, the sensing circuit 316 enters a saturation region when the sensor is in the probe-off state, when the switch 318 closes. For instance, in one configuration, the sensing device 306 comprises an operational amplifier, and when the switch 318 closes (e.g., due to a probe-off condition), the non-inverting terminal of the amplifier that is connected to the output of the first sensing element 302A and the output of the switch 318 is driven to the DC level represented by the node 304. In response, the operational amplifier attempts to set its inverting input to the same DC level as the non-inverting input, causing the amplifier to saturate. The saturation can be readily detected by subsequent componentry to determine a probe-off condition.

Moreover, the output of the sensing device 306 provides both the sensed physiological signal (when the sensor is connected), and an a reliable indication of the sensor connection state. Thus, this technique reduces cost and complexity associated with providing the probe-off functionality. For example, both the sensed signal and the probe-off indication can be communicated from the sensor to the monitor via a single output line, reducing cabling and interface complexity. In another embodiment, the sensor and monitor cable include an additional signal line for communicating the indication of the connection state to the monitor.

In some alternative implementations, the circuit 300 is configured such that the switch 318 or other probe-off componentry affects the frequency of the sensing circuit 306 output instead of, or in addition to, the level of the output voltage. For example, the sensing circuit 306 may output a signal having a predetermined frequency when the sensor is not properly connected to the patient. In such a case, the patient monitor recognizes the predetermined frequency as indicating that the circuit 300 is not properly connected.

In addition, the electrical arrangement of the switch 318 is not limited to the arrangement shown in FIG. 3, and can be coupled to the circuit 300 in a variety of ways. For example, in various embodiments, the switch 318 can be connected to the output of the sensing device 306 or to the negative terminal of the sensing device 306. This arrangement may be used in a configuration where sensing device 306 is located on the sensor 101, for example. In some instances, the output of the switch 318 is coupled to a separate control line that is dedicated to probe-off detection. This arrangement can simplify the processing done by the monitor in making the probe-off determination. In one such case, the separate control line (e.g., the output of the switch 318) is sent directly to the monitor from the sensor via a first lead and the physiological signal (e.g., the output of the sensing device 306) is sent to the monitor via a second lead. In yet another arrangement, the switch is tied to both of the input lines to the sensing device 306 (the outputs of both sensing elements 302A, 302B). In some embodiments, the switch 318 is closed in the probe-off state, and open in the probe-on state. In certain embodiments, the switch 318 is open in the probe-off state, and closed in the probe-on state. Moreover, more than one switch connected in series or in parallel may be used in some other embodiments.

Figure 4:
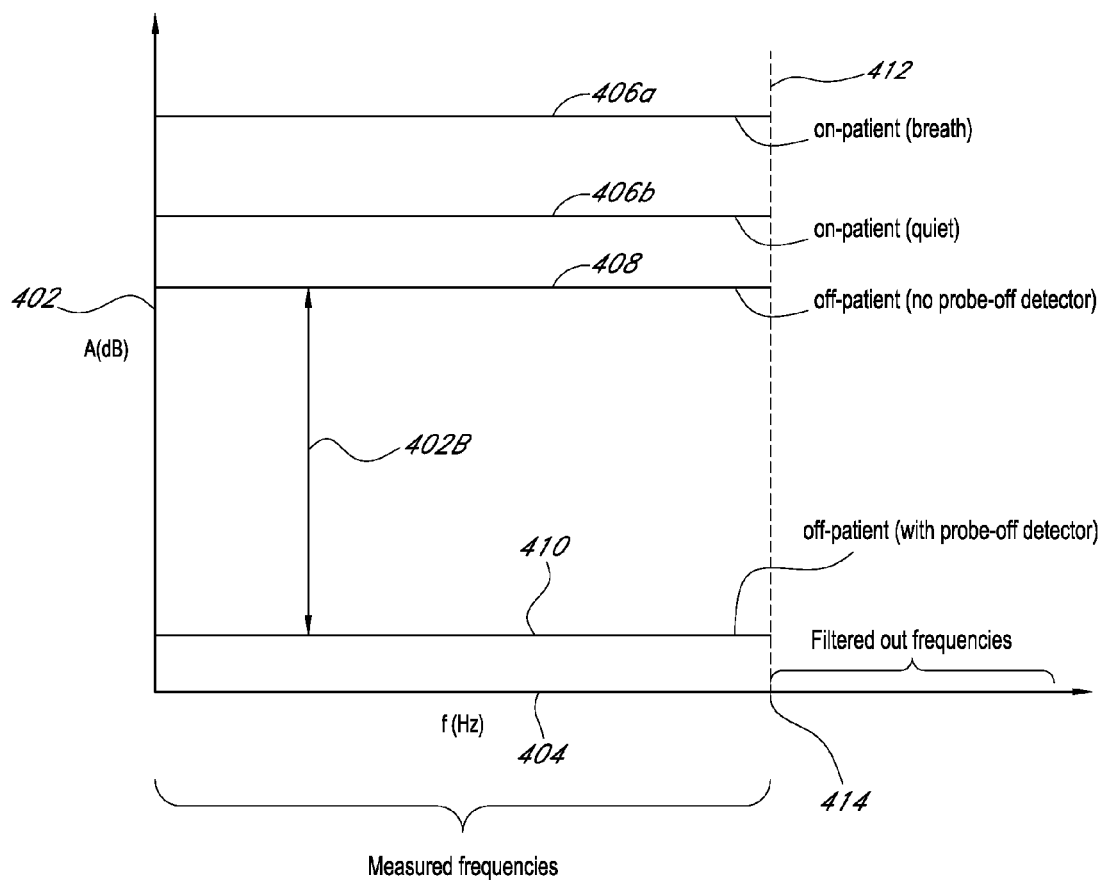
FIG. 4 is a graphical illustration of the output of acoustic physiological sensing circuitry having a probe-off circuit detection circuit in accordance with certain embodiments as compared to the output of sensing circuitry not having a probe-off detection circuit.

FIG. 4 shows a chart 400 including plots 406a, 406b, 408, 410 illustrating output characteristics of example sensing circuitry for example monitoring scenarios. The graph 400 includes an x-axis 402 corresponding to the input frequency of the detected sound signals, and a y-axis 404 corresponding to the amplitude, energy, or other measure of the output signal of the sensor. While the chart 400 will be described with respect to the sensing circuit 300 of FIG. 3 for the purposes of illustration, other compatible sensing circuits may operate in a similar manner.

Referring to FIGS. 3 and 4, in one embodiment, the x-axis 404 corresponds to the frequency of sounds incident on the sensing elements 302A, 302B, while the y-axis 402 corresponds to the detected acoustic signal or a modified version thereof. For example, the y-axis 402 may correspond to an amplified, filtered, attenuated, or otherwise processed version of the detected acoustic signal.

The plot 406a corresponds to the amplitude of the detected acoustic signal when the sensor is attached to the patient and is detecting relatively loud patient bodily sounds, such as breathing or heart sounds. For example, the plot 406 may correspond to the detected acoustic signal or a modified version thereof when the sensor is attached to the patient and the switch 318. The plot 406b, on the other hand, corresponds to the amplitude of the detected acoustic signal when the sensor is attached to the patient and is detecting relatively quiet patient bodily sounds. For example, the plot 406b may represent a situation where the sensor is positioned on a region of the patient (e.g., an appendage) that produces relatively quiet sounds. The plot 406b may alternatively represent a situation where the sensor is positioned on a region of the patient that normally produces relatively loud bodily sounds (e.g., throat or chest), but where the bodily sounds are not currently emanating from the patient, such as where the patient is not breathing.

The plot 408, on the other hand corresponds to the amplitude of the detected signal when the sensor is not attached to the patient, and for an embodiment in which the sensor does not include separate, distinct probe-off componentry. For example, the plot 408 may correspond to the output of the sensing device 306 for an embodiment of the circuit 300 not including the switch 318. In one monitoring scenario, the plot 408 corresponds to a moderate level of environmental noise being detected by a disconnected sensor.

Finally, the plot 410 corresponds to the detected acoustic signal when the sensor is not attached to a patient and where the sensor does include probe-off componentry. For example, the plot 410 corresponds to the detected acoustic signal where the switch 318 is closed.

As discussed, when the sensor is attached to a patient, the output generally corresponds to the detected physiological sounds of the patient. This is true in certain embodiments for input sounds corresponding to sounds in a range of frequencies below a first frequency 414, as indicated by the dotted line 412. For example, sounds below the first frequency 414 may correspond to a desired range of target physiological sounds (e.g., heart, breathing and/or digestive sounds), or to a range of sounds that are otherwise not filtered out by the physiological monitoring system during processing. On the other hand, sounds above the first frequency 414 are filtered out by the system (e.g., by the sensing circuitry 300 or the processing algorithm implemented by the physiological monitor). In one embodiment, the first frequency is about 1 kHz, and the desired range of target physiological sounds correspond to sounds having a frequency of less than about 1 kHz. Other values for the first frequency 414 are possible, such as, for example, about 500 Hz, 1.5 kHz, 2 kHz, 5 kHz, 10 kHz, 50 kHz, 100 kHz, or some other value.

However, as shown by the second plot 408, when the sensor does not include separate, distinct probe-off componentry, the sensor may also produce a relatively highly amplified output signal for desired input frequencies (e.g., below the first frequency 414) even when the sensor is not attached to a patient. For example, the sensor may detect and amplify ambient noise or other sounds at frequencies in the desired range. Because the signal is still amplified significantly, the monitor or user may remain unaware of the probe-off condition and misinterpret the readings made by the sensor. Moreover, to the extent the monitor can determine the quality of the sensor connection, the determination may be relatively difficult to make and may be relatively unreliable.

Thus, it is desirable for the output characteristic of the sensor to provide a clear indication to the monitor (or user) when the sensor is not attached to a patient. For example, the plot 410 indicates that when separate, distinct probe-off componentry is used, the sensing circuitry 300 amplifies the ambient noise (or other un-targeted sounds) for the desired input frequencies much less than where no probe-off componentry is included (plot 408). Because there is a greater differentiation between the output characteristic of the sensor for when the sensor is attached versus when the sensor is not attached, the connection state of the sensor can be more readily determined, reducing erroneous alarms, improving monitoring reliability, etc.

As illustrated by the third plot 410, with the addition of probe-off circuitry, such as that described above with reference to FIG. 3, the detected output is advantageously significantly reduced when the sensor is not connected to the patient. For example, the output is reduced by an amount 402B as compared to embodiments where the sensor does not include probe-off functionality (plot 408), thereby reducing the likelihood of false readings and the like. For example, in one embodiment, the output is reduced by at least about 10 dB.

While the example sensing circuit 300 and the chart 400 have been provided for the purposes of illustration, a variety of compatible alternative configurations are possible. For example, in one embodiment, unlike the illustrated switch 318, the probe-off circuitry does not have a binary ("on", "off") output and instead provides an output having more granularity and corresponding to a degree of the quality of connection.

The mechanism for actuating the switch 318 and the switch 318 can be implemented using a variety of passive, active, electrical, electromagnetic, thermal, mechanical, and/or chemical techniques as mentioned above, with reference to FIG. 2. For example, the switch 318 or any of the switches described herein (e.g., the switches described with respect to FIGS. 5A-7B) may be implemented using a push-button, surface mount switch, transistor, MOSFET, metallic contact, spring, chemical compound, electromagnetic switch, optical switch, thermal switch, thermistor, etc.

Additionally, the circuit 300 may include a single sensing element in some instances, the sensing device 306 may include a different type of amplifier (e.g., a summing amplifier) or may be include some other type of appropriate circuitry for producing the physiological signal.

Example Sensor

Figure 5A:
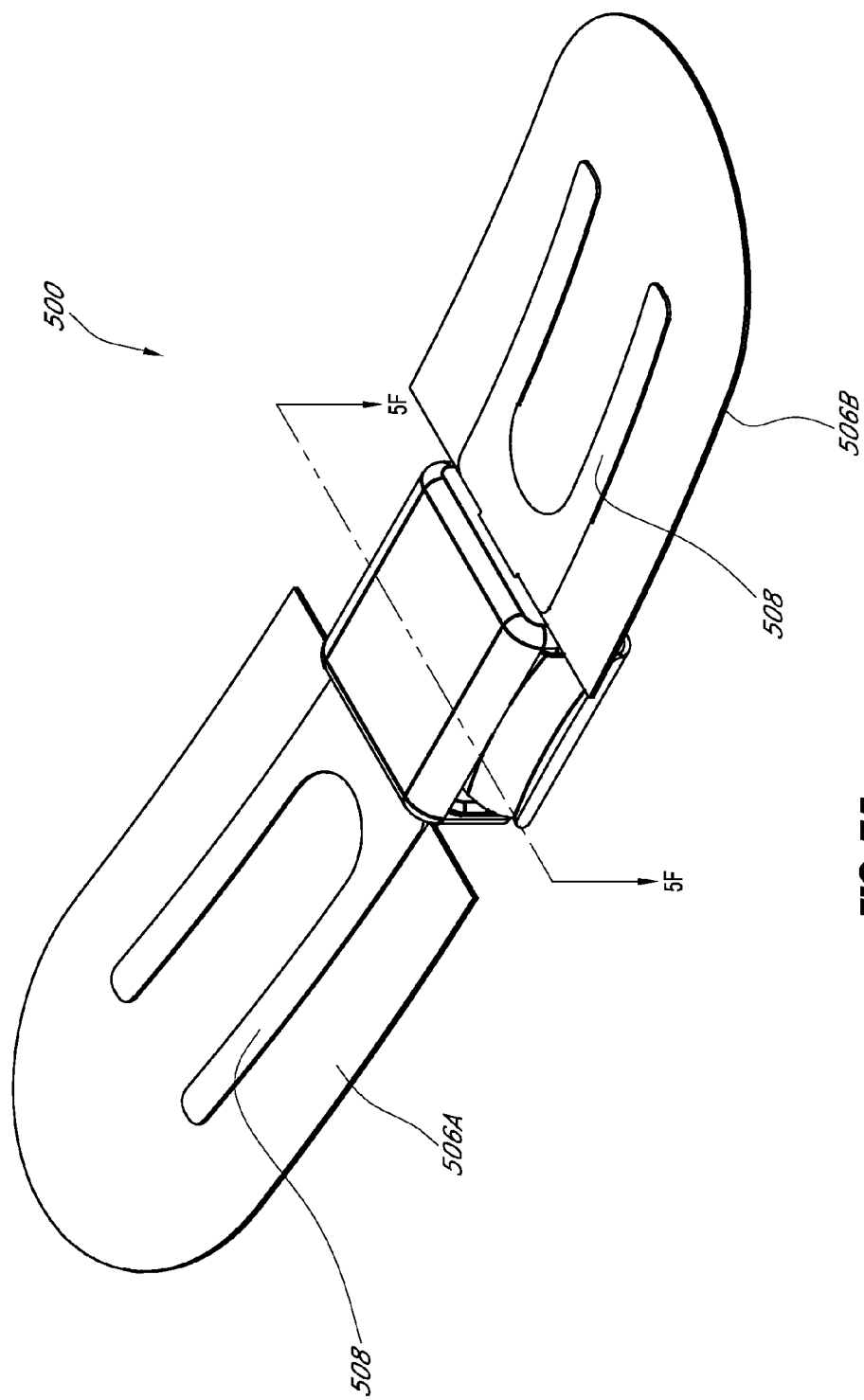
FIG. 5A is a top perspective view illustrating an embodiment of a sensor incorporating probe-off componentry in accordance with embodiments described herein.

FIG. 5A shows a top perspective view of an embodiment of a sensor 500 including probe-off detection capability. The sensor 500 and its corresponding components may be the sensor 101 as shown in FIG. 1C. The sensor 500 includes a sensor cover 501, acoustic coupler 502, and frame 504. The sensor 500 further includes an attachment portion having attachment arms 506A, 506B and a backbone 508, similar to the attachment arms 106, 108 and backbone 110 of FIG. 1C.

Figure 5B:
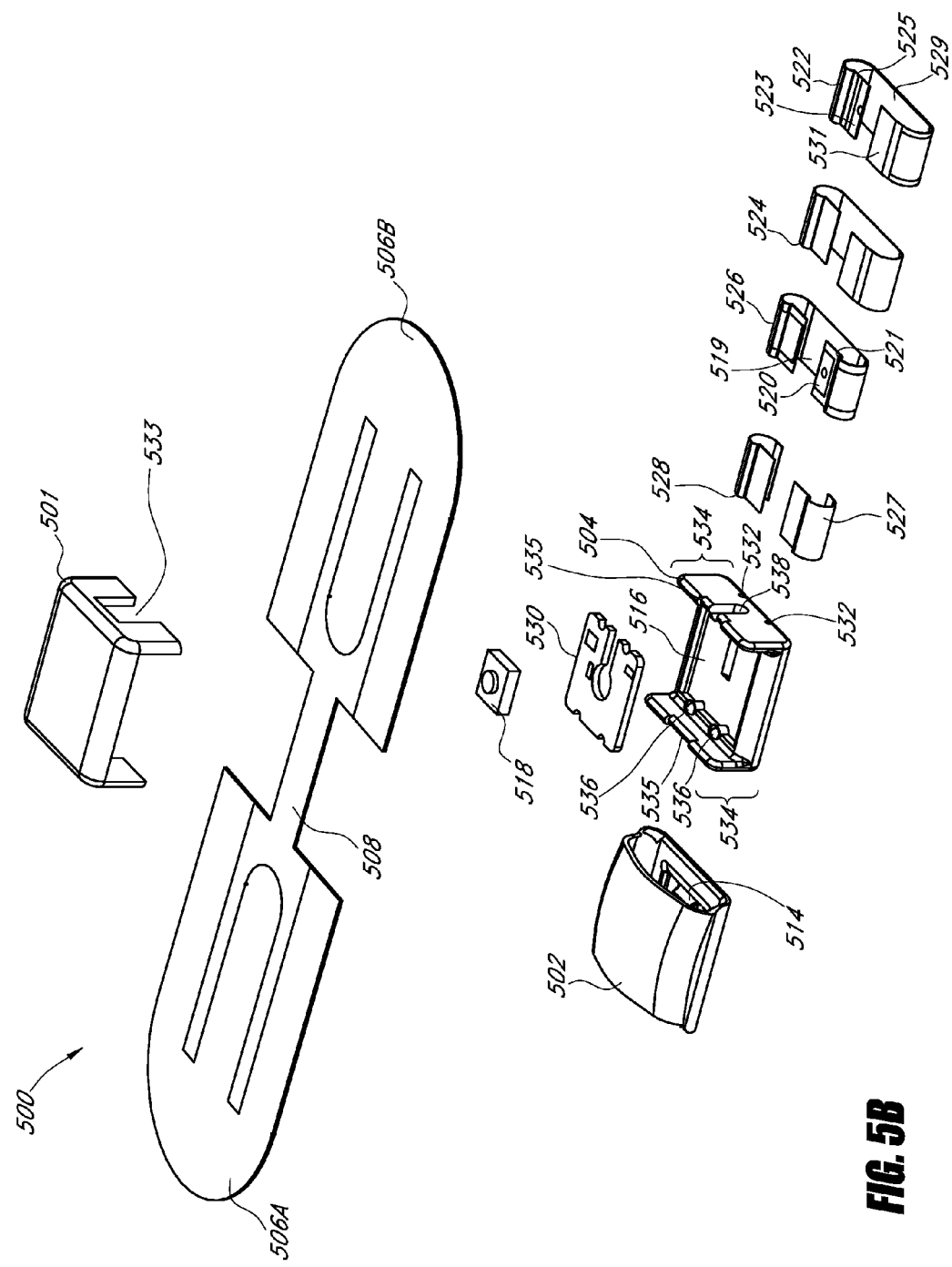
FIGS. 5B-5C are top and bottom exploded perspective views, respectively, of the sensor of FIG. 5A.
Figure 5C:
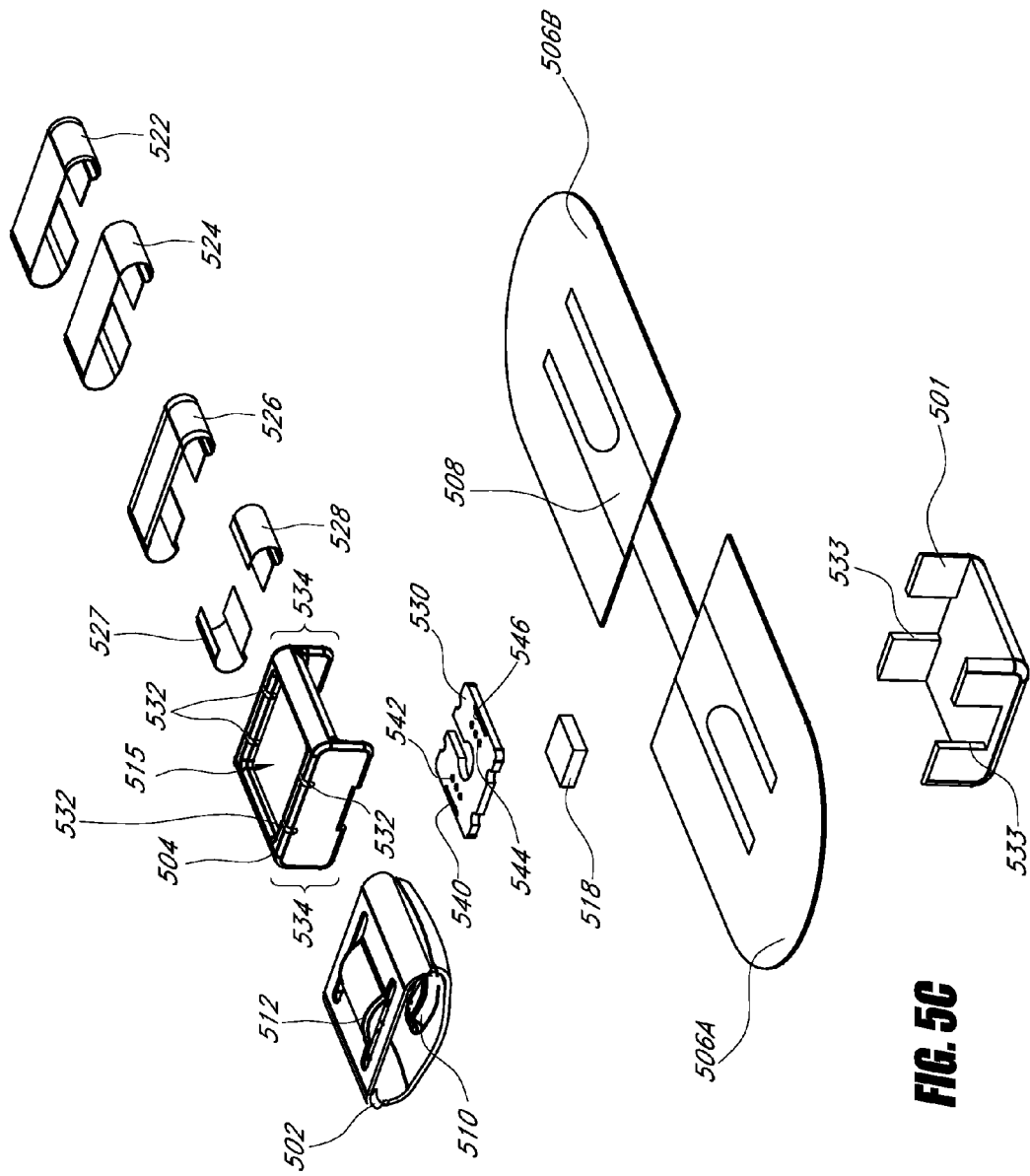

FIGS. 5B-5C illustrate exploded views of the example sensor 500 configured for probe-off detection and to detect acoustic physiological sounds from the patient. The example sensor 500 additionally provides improved signal-to-noise ratio ("SNR") using multiple sensing elements according to techniques described in greater detail in the '931 application, previously incorporated by reference in its entirety. Moreover, the sensor 500 includes a stacked, multiple sensing element configuration providing enhanced shielding and compatible with the techniques described above in greater detail in the '931 application.

The sensor 500 is generally attachable to a patient and can be coupled to a patient monitor. For example, the sensor 500 can be used with the system 10 of FIGS. 1A-1B. Moreover, the sensor 500 can be compatible with the sensor system 100 of FIG. 1C, and may be the sensor 101 of FIG. 1C.

Referring to FIG. 5B, the sensor 500 of certain embodiments includes an acoustic coupler 502, a printed circuit board (PCB) 530, a frame 504 with riser portions 534, first and second acoustic sensing elements 522, 526, and multiple adhesive layers 524, 527, 528. The sensor can further include a cover or shell 501. The acoustic coupler 502 houses the frame 504, which is generally configured to support various components of the sensor 500 in an assembled state, including the PCB 530, switch 518, sensing elements 522, 526, and adhesive layers 524, 527, 528. The sensing elements 522, 526, are piezoelectric films in the illustrated embodiment, although other types of sensing elements can be used. Moreover, while the sensor 500 includes multiple sensing elements beneficially arranged for improved sensing, the probe-off functionality and other aspects described herein are generally compatible with other designs, including single-sensing element designs. Further example sensing elements are described in both the '931 and '939 applications, and are explicitly incorporated by reference herein.

Furthermore, the sensor 500 includes a switch 518 configured to provide an indication of the integrity of the connection state of the sensor. The sensor 500 may include sensing circuitry, such as the sensing circuit 300 shown in and described above with respect to FIG. 3, for example, and the switch 518 may correspond to the switch 318 of FIG. 3.

The switch 518 is positioned in an upper cavity 516 (FIG. 5A) of the frame 504 above the PCB 530 such that the underside of the switch 518 comes in contact with an upper portion of the PCB 530. The switch 518 is advantageously spaced away from the skin (e.g., on top of the PCB 530 and below the coupler 502, as shown), which can increase reliability in probe-off detection. Where the switch 518 or other probe-off componentry are not spaced from the skin, but are instead placed in proximity to or touching the skin, there may be an increase in false probe-off readings. For example, in some cases the elasticity of the skin may allow the switch 518 to toggle even when the sensor 500 is properly attached to the patient. However, in some embodiments, the switch 518 can be placed in proximity to the skin.

Furthermore, placement of the switch 518 and/or other components of the probe-off assembly away from active portions of the sensor which interact with the patient (e.g., the membranes 522, 526 and bottom portions of the coupler 502 and frame 504) can provide certain advantages. For example, the switch 518 in certain embodiments faces in a direction that is substantially opposite the patient contact surface of the sensor 500. For example, the switch 518 faces generally opposite the underside of the coupler 502, frame 504 and/or sensing elements 522, 526. In this manner, when the sensor 500 is attached to the patient's skin, actuation forces incident on the switch 518 are in the direction of the patient's skin, rather than away from the patient's skin. Thus, actuation of the switch 518 will tend to improve the coupling between the patient and sensor 500 rather than tending to separate the patient and the sensor 500. For example, such an arrangement can reduce the risk that the probe-off detection components will interfere with the active portions of the sensor, or vice versa, improving the accuracy and reliability of both probe-off detection and physiological measurement. Such placement can also reduce the risk that the probe-off componentry will become soiled or otherwise damaged from frequent interaction with the patient's skin, improving reliability. In some alternative embodiments, however, the switch 518 or other components of the probe-off assembly are placed on or near the skin or near the active portions of the sensor 500.

In the illustrated embodiment, the switch 518 is electrically closed when the button is depressed, causing the sensing circuitry (not shown) to provide an indication that the sensor is in an unattached state. Once the sensor 500 is attached to a patient, the push-button releases, and the switch 518 electrically opens, allowing the sensor to output the detected physiological parameters. In another embodiment, the push button of the switch 518 releases in the unattached state and is depressed in the attached state.

Although illustrated as a push-button mechanical switch, the probe-off componentry can include a variety of different types of components instead of, or in addition to such a switch. Examples of some such alternative components are described above with reference to FIGS. 2 and 3. In one embodiment, the backbone 508 includes a strain gauge configured to provide an output signal corresponding to an amount or characteristic of the flex in the backbone 508. The output signal can be used to determine the attachment state of the sensor 500.

The coupler shell 502 is generally configured to transmit vibrations received from the patient to the films 522, 526 in the piezoelectric stack. The acoustic coupler 502 can include a lower exterior protrusion or bump 512 (FIGS. 5C, 5D) configured to press against the patient's body when the acoustic sensor 500 is fastened into place on the patient. The acoustic coupler 502 can also include a lower interior protrusion 514 (FIGS. 5B, 5D) designed to abut against the films 522, 526 and to bias them in tension across the acoustic cavity 515 (FIG. 5B).

The coupler 502 can further form a part of the probe-off componentry. For example, the coupler 502 includes an upper interior protrusion 510 (FIGS. 5C, 5D) designed to interact with the backbone 508 and the attachment arms 506A, 506B to toggle the switch 518, depending on the attachment state of the sensor 500.

Figure 5D:
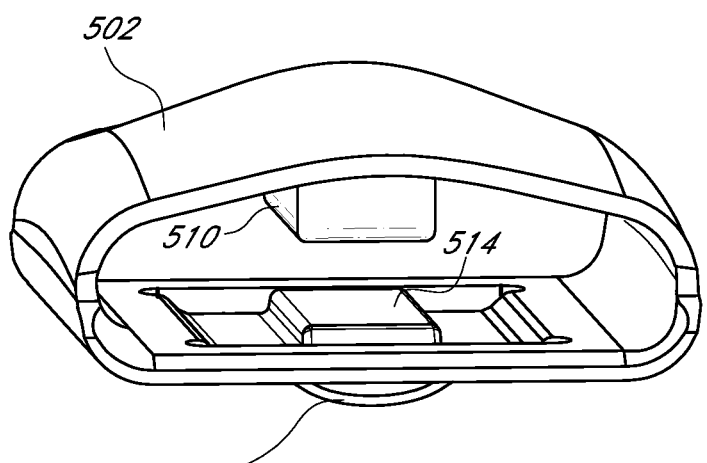
FIG. 5D is a side perspective view illustrating the acoustic coupler of the sensor of FIGS. 5A-5C.
Figure 6A:
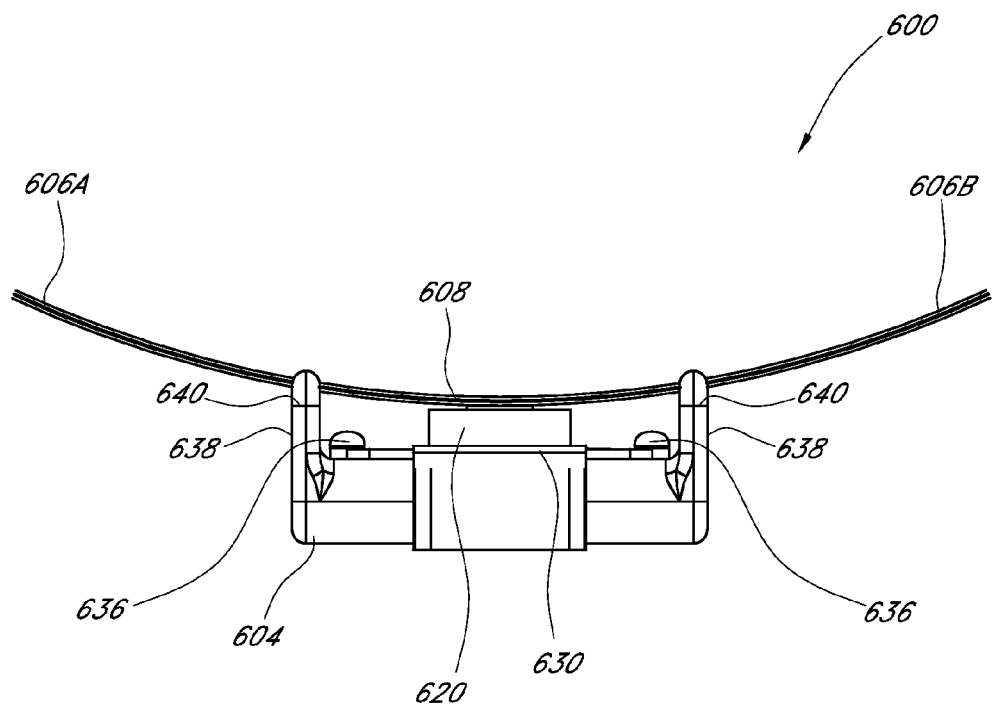
FIG. 6A is a side perspective view illustrating an embodiment of a sensor in a sensor-off configuration.

Referring to FIGS. 5A and 6A, the attachment arms 506A, 506B, 606A, 606B (and the distal portions of the backbone 508, 608 which extend into the attachment arms 506A, 506B, 606A, 606B, respectively) are biased upwards with respect to the sensor 600 in the unattached state. This is due to interior protrusion 510 of the coupler 502 (FIG. 5D) abutting and exerting a downward force on the middle portion of the backbone 508, 608. For example, during assembly, the coupler 502 is stretched around the frame 504, 604 and over the backbone 508, 608 which extends across the frame 504, 604 and sits in the cutouts 535. When the coupler 502 is allowed to "snap" or return back into its original shape, the inner protrusion 510 of the coupler 502 presses against the middle portion backbone 508, 608, thereby causing the backbone 508, 608 to flex. The downward force also causes the center portion of the backbone 508, 608 to depress the switch 518, 620 in the default, detached configuration (FIGS. 5A and 6A). As such, the sensor 500, 600 outputs a signal indicating the probe-off condition. Moreover, the cutouts 535 on the frame 504, 604 exert a corresponding upward force on the portions of the backbone 508, 608 that rest on the notches 535 (FIG. 5B) of the frame 504, 604 causing the arms 506A, 506B, 606A, 606B to flex upwards.

Figure 6B:
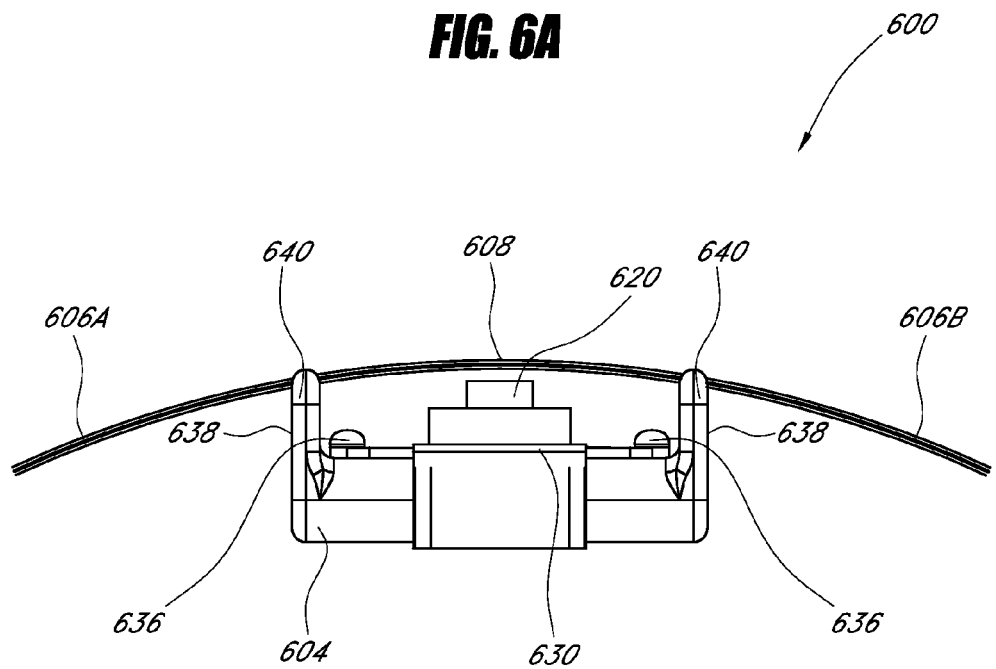
FIG. 6B is a side perspective view illustrating an embodiment of a sensor in a sensor-on configuration.

Conversely, as the attachment arms 506A, 506B, 606A, 606B are brought into contact with the patient during attachment of the sensor 500, 600 to the patient, the backbone 508, 608 flexes in generally the opposite direction. In this state, the center portion of the backbone 508, 608 exerts an upward force against the upper interior protrusion 510 of the coupler 502, causing the switch 518, 620 to release (FIG. 6B). The sensor then outputs a signal indicating that the sensor is properly attached to the patient.

The above-described flexed configuration provides a robust probe-off detection mechanism. For example, due to the flexed configuration, the attachment arms 506A, 506B, 606A, 606B and the center portion of the backbone 508, 608 travel an increased distance during the transition from the unattached state to the attached state (FIGS. 6A and 6B). Moreover, the backbone 508, 608 may generally "snap" between the two flexed configurations. The increased travel and/or snapping behavior can cause the backbone 508, 608 to have two relatively discrete mechanical states based on the attachment state of the sensor. As such, the backbone 508, 608 will toggle the switch in a relatively reliable manner when the sensor is attached and detached from the patient.

The coupler shell 502 can be similar to any of the acoustic couplers described in greater detail in the '931 application, for example. Use of the coupler to bias the backbone 508, 608 and actuate the switch 518, 620 can reduce the complexity of manufacturing process and/or the design of the switch 518, 620 and can reduce the number of parts used to implement the probe-off capability. However, other compatible designs incorporate additional components to bias the backbone 508 and actuate the switch 518, 620.

Referring to FIG. 5A, the sensor cover or shell 501 fits over the acoustic coupler 502 of the assembled sensor 500, and has notches, or cutouts 533, for the backbone 508 and the attachment arms 506A, 506B. The cover 501 is formed of a relatively rigid material (e.g., plastic) in some cases. The sensor cover 501 provides additional protection for the sensor 500. For example, the cover 501 can prevent unwanted interaction with the probe-off componentry, reducing the risk of possible probe-off detection errors. For example, as discussed, when the sensor is in an attached state, the button 520 on the switch 518 is released. Without the cover 601, if the patient, medical personnel or other source were to push down on the top of the acoustic coupler 502, the coupler 502 and backbone 508 could move downwards, depressing the button 520. The sensor would then improperly indicate that the sensor was in an unattached state. The cover 601 reduces the likelihood of such a situation occurring by providing a relatively rigid barrier between the external environment and the coupler 502.

The remaining components of the sensor 500 can be assembled similarly to the sensors described in the '931 application. For example, the first piezoelectric film 526 is wrapped around a portion of the frame 504 and extends across an acoustic cavity 515 (FIG. 5B) of the frame 504 in tension. When assembled, the adhesive portions 527, 528 are positioned between interior opposing sides of the first film 526 and corresponding sides of the sensor frame 504, thereby adhering the first film 526 in place with respect to the frame 504.

The adhesive layer 524 is wrapped around the first sensing element 526, and the second sensing element 522 is in turn wrapped around the adhesive layer 524, generally forming a piezoelectric stack. As discussed in greater detail in the '931 application, the active portions of the films 522, 526 that extend across the acoustic cavity 515 (FIG. 5B) are thus generally free to move in response to received vibrations, enabling detection of a physiological signal when the sensor 500 is in an attached state. In certain embodiments, the acoustic cavity 515 (FIG. 5B) or a portion thereof extends all the way through the frame 504. For example, the cavity may form one or more holes in the interior portion of the frame 504.

The PCB 530 is positioned in the upper cavity 516 (FIG. 5A) such that the underside of the PCB 530 comes into contact with the regions 523, 525 of the second film 522 and the regions 520, 521 of the first film 526. The flap 531 of the second film 522 rests on top of the PCB 530 in the illustrated embodiment, allowing electrical coupling of the first sensing element 526 to the PCB 530 and associated circuitry.

Generally, the piezoelectric films 522, 526 can be any of those described herein. In the illustrated embodiment, for example, the films 522, 526 are the piezoelectric films described in greater detail in the '931 application, previously incorporated by reference in its entirety, having flooded electrode surfaces 519, 529, respectively, which form the outer surfaces of the piezoelectric stack. Moreover, the films 522, 526 include one or more vias or through holes extending an electrode from one surface of the films 522, 526 to a corresponding region 520, 523 on the opposing surface of the respective film 522, 526. As discussed above, this configuration enables coupling of the four electrodes (e.g., the anode and cathode for each film 526, 522) to the appropriate contacts on the underside of the PCB 222.

For example, in one embodiment, the region 525 (FIG. 5B) of the flooded cathode coating on the outer surface of the second film 522 touches one or more of the contacts 546 on the underside of the PCB 530 (FIG. 5C Meanwhile, the through-holed region 523 (FIG. 5B) of the outer surface of the second film 522, which includes an anode coating, touches the contact 544 on the underside of the PCB 530 (FIG. 5C). Regarding the first film 526, the region 521 (FIG. 5B) of the cathode coating touches one or more of the contacts 540 on the underside of the PCB 530 (FIG. 5C). Meanwhile, the through-holed region 520 (FIG. 5B) of the inner surface of the first film 526, which includes an anode coating, touches one or more of the contacts 542 on the underside of the PCB 530 (FIG. 5C).

According to the above-described connection scheme, the films 522, 526 can be coupled to circuitry (not shown) residing on the PCB 222 or other system component (e.g., the hub or monitor) to provide improved SNR and/or electrical shielding. For example, the electrodes of the films 522, 526 can each be coupled to an input of an attenuation circuit (e.g., a differential amplifier) or ground (or other common potential), such as in the manner illustrated schematically with respect to FIG. 3 above. Specifically, although other connections schemes are possible, in one embodiment, the contact 540 (FIGURE C) on the PCB 530 couples the flooded, outer cathode of the second, exterior film 522 to ground, and the contact 544 couples the outer, flooded anode of the first, interior film 526 to ground. Moreover, the contacts 544 couple the inner, un-flooded anode of the second, exterior film 522 to a first (e.g., positive) terminal of a difference amplifier or other noise attenuation circuit. Finally, the contacts 542 couple the un-flooded, inner cathode of the first, interior film 526 to a second (e.g., negative) terminal of the difference amplifier.

The frame 504 can include one or more pressure equalization pathways 532. The pressure equalization pathways 532 provide an air communication pathway between the lower acoustic cavity 515 and ambient air pressure, and allow the sensor's membrane(s) or film(s) 522, 526 to vibrate within the acoustic cavity 515 independent of skin elasticity or the force used to attach the sensor to a patient's skin. Further examples of pressure equalization pathways 532 are described in the '931 application, and are explicitly incorporated in their entirety by reference herein.

FIG. 5D shows a side perspective view of an embodiment of an acoustic coupler 502. As mentioned previously, the acoustic coupler 502 is configured to transmit vibrations received from the patient to the sensor membranes 522, 526, and houses the frame 504 and various components of the sensor including the switch 518, PCB 530, sensor membranes 522, 526 and adhesive layers 524, 527, and 528. The acoustic coupler 502 may be made of a flexible, resilient, substance that is easily stretched or otherwise manipulated but returns to its original shape when no force is exerted against it. Possible materials may include, but are not limited to rubber, silicone, and other elastomers.

Figure 5E:
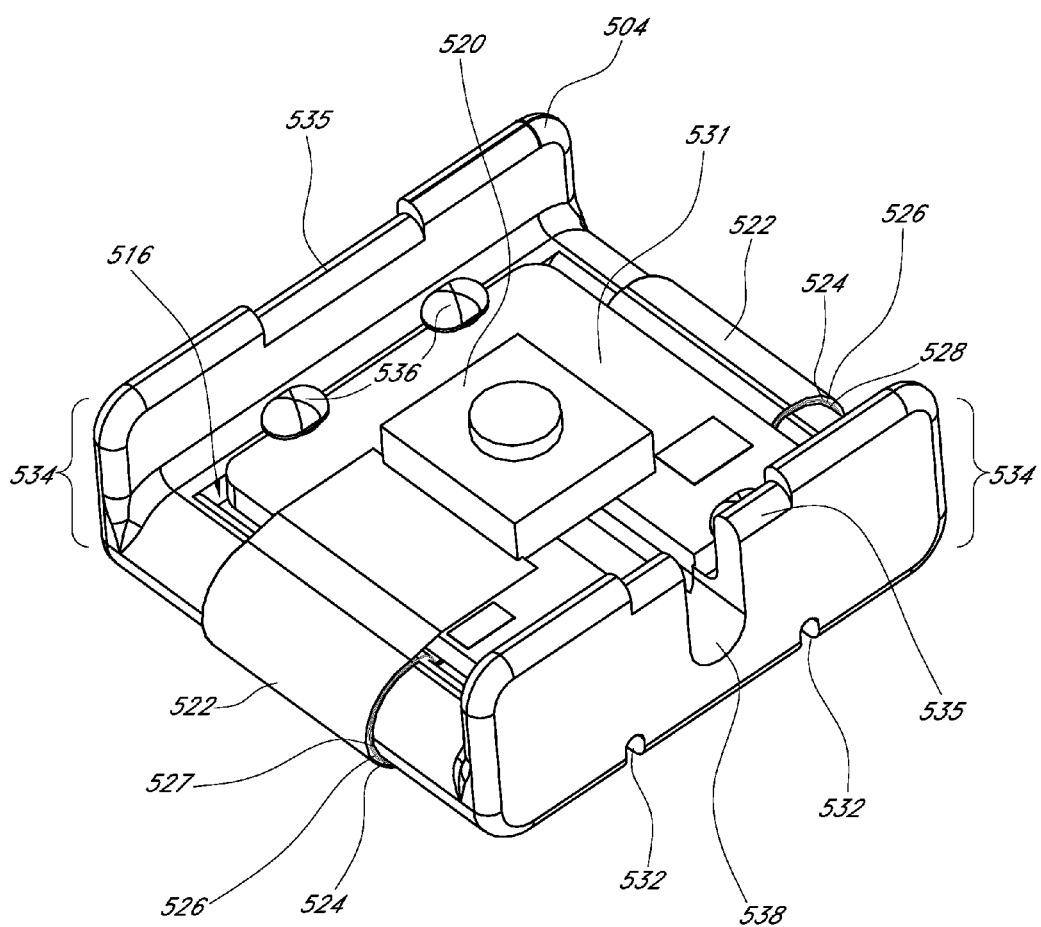
FIG. 5E is a side perspective view illustrating the sensor of FIGS. 5A-5C with the acoustic coupler and backbone removed.

FIG. 5E shows a side perspective view of the sensor 500 assembled, with the coupler 502, attachment arms 506A, 506B, and backbone 508 removed. The frame 504 includes riser portions 534 with notches, or cutouts 535, where the backbone 508 and attachment arms 506A, 506B rest when assembled. The frame 504 also includes a pathway 538 for a wire (not shown) to be coupled with the PCB 530. As discussed previously, the frame 504 further includes equalization pathways 532. Resting in the cavity 516 of the frame 504 lies the PCB 530, secured by posts 536. As mentioned above, with respect to FIGS. 5B and 5C, the sensor membranes 522, 526 and adhesive layers 524, 527, 528 are wrapped around the frame 504. The switch 518 sits atop the PCB 530 and sensor membrane 522. As mentioned previously, when the sensor 500 is in an unattached state, a downward force is exerted on the switch 518 by the upper interior portion 510 of the acoustic coupler 502, the attachment arms 506A, 506B and the backbone 508.

Figure 5F:
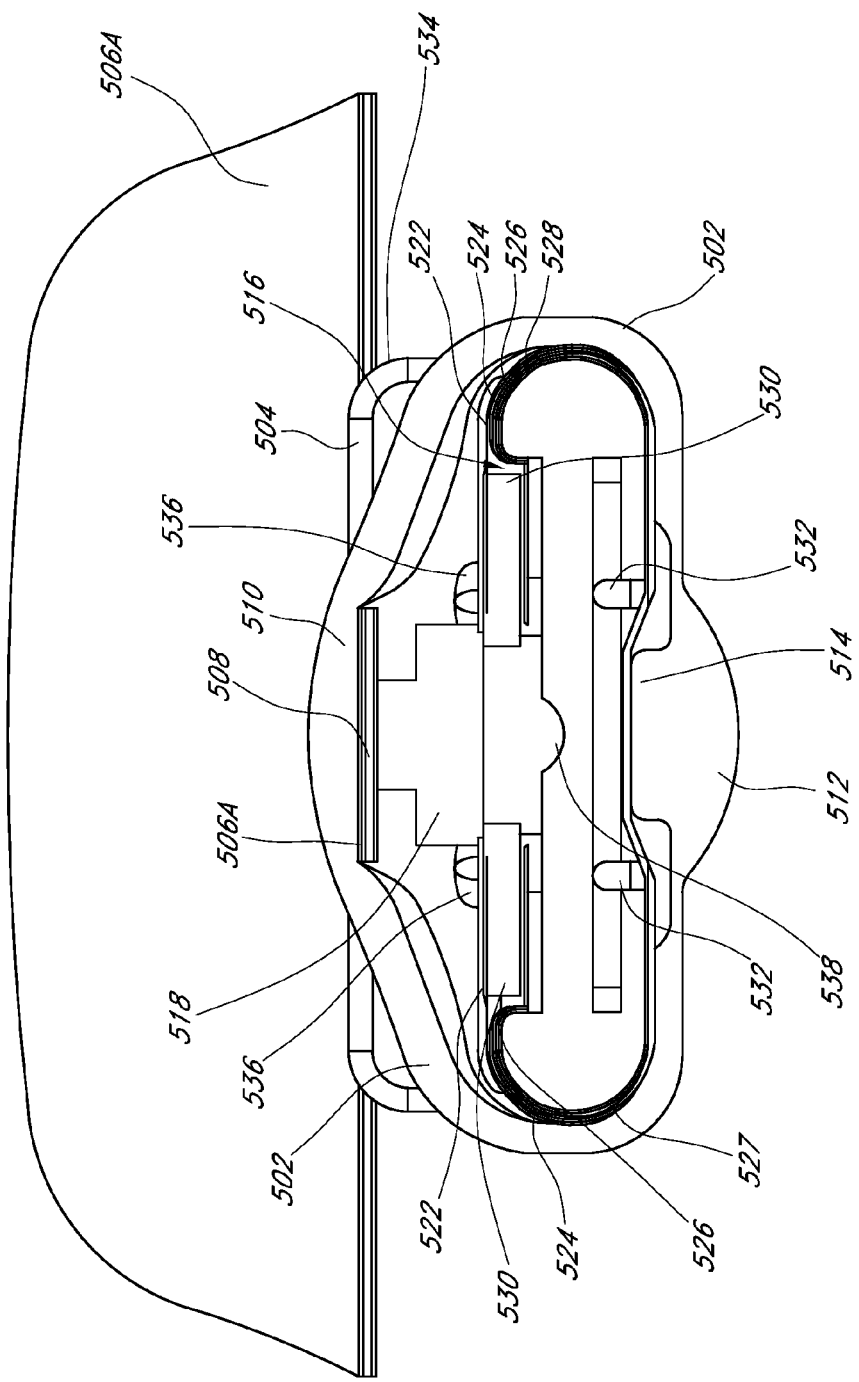
FIG. 5F is a partial cross-sectional view illustrating the sensor of FIGS. 5A-5C along the dotted line shown in FIG. 5A.

FIG. 5F, shows a cross-sectional view of an embodiment of the assembled sensor 500 along the line 5F, illustrated in FIG. 5A. In FIG. 5F, the protrusion 510 of the coupler 502 urges the middle portion of the backbone 508 downward, depressing the switch. Downward movement of the attachment arms would cause the protrusion 510 to compress and/or cause the coupler 502 to stretch upwards with respect to the frame, allowing the switch 518 to release (FIG. 6B).

FIG. 5F further illustrates the placement of the various components of the sensor 500 in relation to each other in the assembled state. For example, the adhesives 527, 528 wrap around rounded ends of the frame 504. The first sensor membrane 526 wraps around the adhesives 527, 528, and the adhesive 524 wraps around the first sensor membrane 526. Finally, a second sensor membrane 522 wraps around the adhesive 524. The PCB 530 is secured by posts 536 to the frame 504, and sits within the cavity 516 atop the wrapped sensor membranes 522, 526 and adhesives 524, 527, 528. The switch 518 sits atop the PCB 530.

FIG. 5F further illustrates the groove 538 formed in the frame 504 for accommodating the cable (not shown) and the frame equalization pathways 532, described previously. Furthermore, FIG. 5F illustrates the lower exterior protrusion 512 of the acoustic coupler 502 configured to improve the coupling between the source of the signal and the sensing element, and the lower interior protrusion 514 of the acoustic coupler 502 creating tension in the sensor membranes 522, 526, and adhesive 524.

FIGS. 6A-6B described above show side perspective views of a sensor 600 in detached and attached states, respectively. The sensor 600 is similar to the sensor 500 of FIGS. 5A-5F, and includes attachment arms 606A, 606B, a backbone 608, a frame 604 having riser portions 638 with notches 640, and a switch 620. For the purposes of illustration, the sensor is shown without the cover and acoustic coupler with the PCB 630 secured to the frame 604 by posts 636.

Additional Embodiments

Figure 7A:
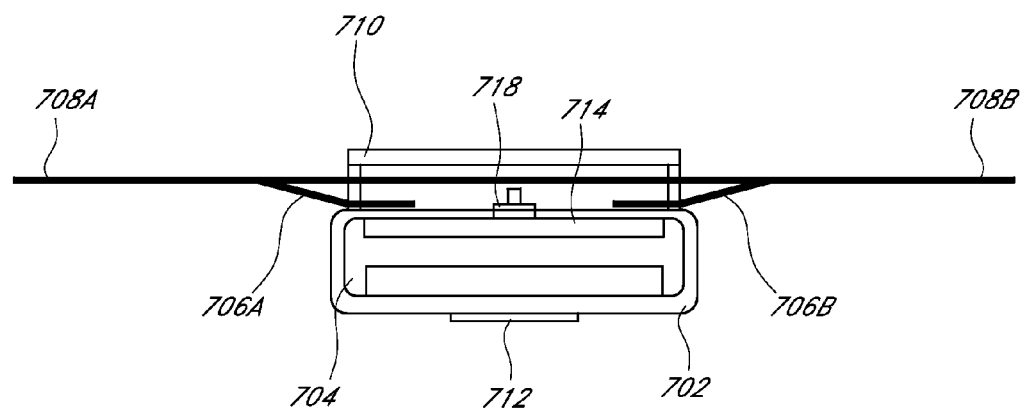
FIGS. 7A-7B and 8A-8B illustrate side perspective views of additional embodiments of sensors including probe-off componentry.
Figure 7B:
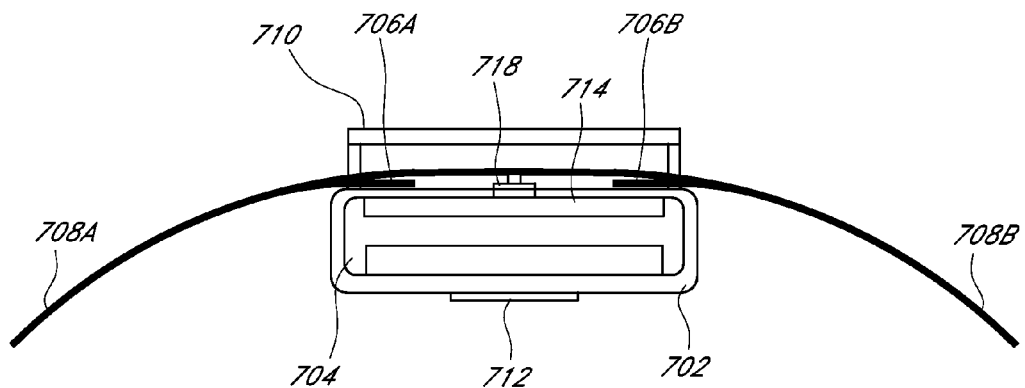

FIGS. 7A-7B and 8A-8B are side perspective views of additional embodiments of the sensor described above. FIGS. 7A-7B are block diagrams illustrating a sensor 700 wherein the springs 706A, 706B are used to toggle the switch 718, depending on the attachment state of the sensor 700. FIG. 7A illustrates the sensor 700 in an unattached state, and FIG. 7B illustrates the sensor 700 in an attached state.

Similar to sensor 500 of FIGS. 5A-5F, sensor 700 includes an acoustic coupler 702 with a lower exterior protrusion 712, frame 704, attachment arms 706A, 706B, a sensor cover 710, and a switch 718 placed on a PCB 714, all of which are described in greater detail above. Although not illustrated in FIGS. 7A and 7B, the sensor 700 can further include a piezoelectric stack, described in greater detail above, additional protrusions in the coupler, and other components described above with reference to FIGS. 5A-5F. Additionally, the sensor 700 includes springs 706A, 706B. A proximal side of the springs 706A, 706B is attached to the PCB 714, the frame 704 and/or the coupler 702. A distal side of the springs 706A, 706B is attached to an underside of the attachment arms 708A, 708B.

Moreover, when in an unattached state, the springs 706A, 706B exert an upward force against the attachment arms 708A, 708B, respectively. The upward force from the springs 706A, 706B raises the attachment arms 708A, 708B and the sensor cover 710. The upward force also urges the attachment arms 708A, 708B and the cover 710 upward, preventing them from contacting the switch 718. In this configuration, the switch 718 is released, causing the sensing circuitry (not shown) to output an indication that the sensor is in an unattached state. The attachment arms can be configured similar to the attachment arms and/or the backbone described above with reference to FIGS. 5A-5F, 6A, and 6B. Furthermore, the attachment arms 708A, 708B can be upward biased similar to the attachment arms and backbone described above with reference to FIGS. 5A-5F, 6A, and 6B.

FIG. 7B is a side perspective view of the sensor 700 illustrating the situation where the sensor 700 is in an attached state, and where the spring 706A, 706B and distal portions of the attachment arms 708A, 708B are therefore downwardly biased, exerting a downward force against the switch 718. When placing the sensor 700 in an attached state, the attachment arms 708A, 708B are biased downward with sufficient force to overcome the inherent upward bias of the springs 706A, 706B. The distal portions of the attachment arms 708A, 708B can be affixed to a patient using an adhesive on the underside of the attachment arms 708A, 708B. As the distal portions of the attachment arms 708A, 708B are biased downwards, the space between the switch 718 and attachment arms 708A, 708B decreases until the middle portion of the attachment arms 708A, 708B exert a downward force against the switch 718. The downward force of the attachment arms 708A, 708B on the switch 718 closes the switch 718, and causes the sensing circuitry (not shown) to output an indication that the sensor 700 is in an attached state and/or allows the physiological parameters to be monitored.

Figure 8A:
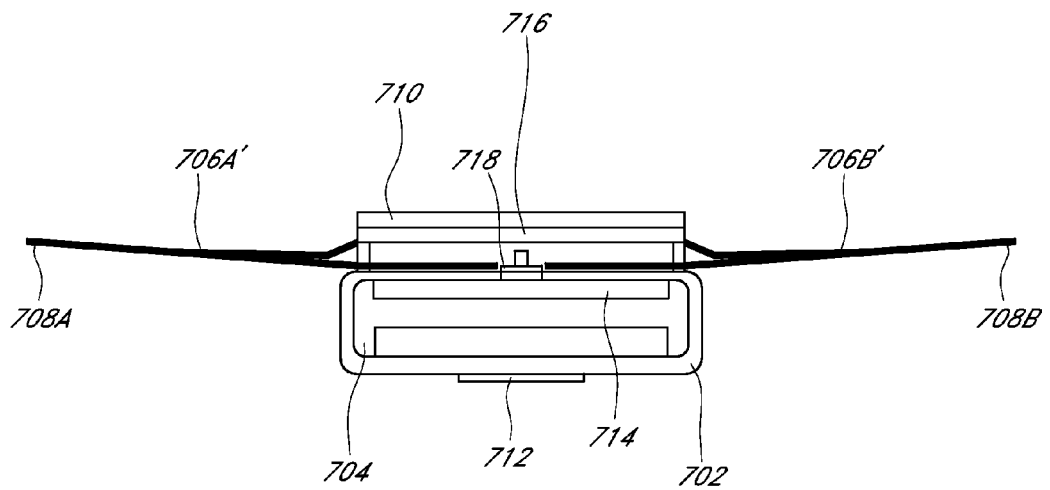
Figure 8B:
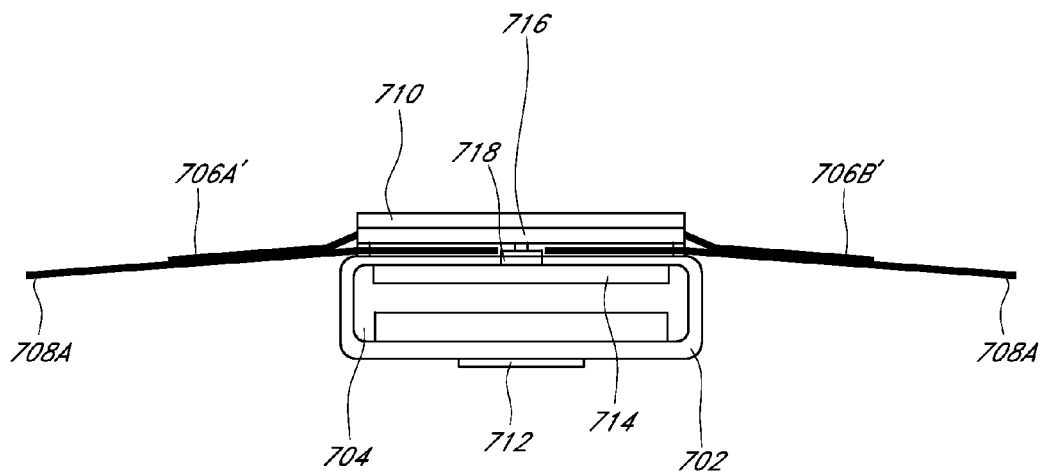

FIGS. 8A and 8B illustrate additional embodiments of sensor 700. For instance, in FIGS. 8A and 8B sensor 700 further includes a plastic plate 716, and the springs 706A', 706B' are located above the attachment arms 708A, 708B and connect to the topside of attachment arms 708A, 708B. The attachment arms can be constructed similar to the attachment arms above with reference to FIGS. 7A and 7B. Furthermore, the attachment arms 708A, 708B can be upward biased similar to the attachment arms and backbone described above with reference to FIGS. 5A-5F, 6A, and 6B.

FIG. 8A illustrates the sensor 700 in a situation when it is not in an attached state. In this situation, the plastic plate 716 and cap 710 reside above the coupler 702 and switch 718. The springs 706A', 706B' extend outwardly from the plastic plate 716 and are attached to the topside of distal portions of the attachment arms 708A, 708B. The switch 718 can be located above, below or protrude through a hole of the attachment arms 708A, 708B. The springs 706A', 706B' are upwardly biased causing an upward force to be exerted on the attachment arms 708A, 708B, forcing the distal portions of the attachment arms 708A, 708B upward. The space between the plastic plate 716 and the switch 718 allows the switch 718 to release, causing the sensing circuitry (not shown) to output an indication that the sensor 700 is in an unattached state.

FIG. 8B illustrates the sensor 700 in an attached state. When the sensor 700 is placed in an attached state, the attachment arms 708A, 708B are biased downward with sufficient force to overcome the inherent upward bias of the springs 706A, 706B. The distal portions of the attachment arms 708A, 708B can be affixed to a patient using an adhesive on the underside of the attachment arms 708A, 708B. As the distal portions of the attachment arms 708A, 708B are biased downwards, the space between the switch 718 and plastic plate 716 decreases until the plastic plate 716 exerts a downward force against the switch 718. The downward force of the plastic plate 716 on the switch 718 closes the switch 718 and causes the sensing circuitry (not shown) to output an indication that the sensor 700 is in an attached state and/or allows the physiological parameters to be monitored. Alternatively, when the attachment arms 708A, 708B are positioned above the switch 718, the attachment arms 708A, 708B can be used to exert a downward force on the switch 718.

Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. An acoustic sensor configured to non-invasively detect acoustic vibrations associated with a medical patient, said acoustic vibrations indicative of one or more physiological parameters of the medical patient, said acoustic sensor comprising:
   a sensor support;
   at least one sound sensing membrane supported by the sensor support and configured to detect acoustic vibrations associated with a medical patient and produce a membrane signal corresponding to the acoustic vibrations based at least in part on an attached state of the acoustic sensor; and
   a probe-off assembly supported by the sensor support, the probe-off assembly configured to produce a probe-off signal responsive to the attached state of the acoustic sensor and/or to a detached state of the acoustic sensor, wherein at least a portion of the sensor support is between a patient contact surface of the acoustic sensor and the probe-off assembly.

2. The acoustic sensor of claim 1, wherein the probe-off signal indicates a sensor connected condition based at least in part on the attached state of the acoustic sensor and a sensor not connected condition based at least in part on the detached state of the acoustic sensor.

3. The acoustic sensor of claim 1, wherein the probe-off signal is indicative of an integrity of a connection between the acoustic sensor and the medical patient.

4. The acoustic sensor of claim 1, wherein the probe-off assembly comprises a switch configured to actuate in response to the attached state of the acoustic sensor.

5. The acoustic sensor of claim 1, wherein the probe-off assembly is positioned to actuate in response to a force that is in a direction of the medical patient's skin to place the acoustic sensor in the attached state.

6. The acoustic sensor of claim 1, wherein a physiological monitor in communication with the acoustic sensor is responsive to the probe-off signal to determine a sensor connected condition or a sensor not connected condition.

7. The acoustic sensor of claim 6, wherein the acoustic sensor comprises an output that is responsive to both the membrane signal and to the probe-off signal.

8. The acoustic sensor of claim 7, wherein a sensing circuit responsive to the output produces a sensor signal indicative of an integrity of a connection between the acoustic sensor and the medical patient and based at least in part on the acoustic sensor being in the attached state corresponds to the acoustic vibrations detected by the sensing membrane.

9. The acoustic sensor of claim 8, wherein the sensing circuit is located on a cable positioned between the acoustic sensor and the physiological monitor, wherein the cable communicatively couples the acoustic sensor to the physiological monitor.

10. An acoustic sensor configured to non-invasively detect acoustic vibrations associated with a medical patient, said acoustic vibrations indicative of one or more physiological parameters of the medical patient, said acoustic sensor comprising:
- a sensor support;
- at least one sound sensing membrane supported by the sensor support and configured to detect acoustic vibrations associated with a medical patient and produce a membrane signal corresponding to the acoustic vibrations based at least in part on an attached state of the acoustic sensor; and
- a probe-off assembly supported by the sensor support, the probe-off assembly configured to produce a probe-off signal responsive to the attached state of the acoustic sensor and to a detached state of the acoustic sensor,
- wherein a mechanically active portion of the at least one sound sensing membrane configured to move in response to the acoustic vibrations is further configured to be located between the medical patient's skin and the probe-off assembly when the sensor is in the attached state.

11. An acoustic sensor configured to non-invasively detect acoustic vibrations associated with a medical patient, said acoustic vibrations indicative of one or more physiological parameters of the medical patient, said acoustic sensor comprising:
- a sensor support;
- at least one sound sensing membrane supported by the sensor support and configured to detect acoustic vibrations associated with a medical patient and produce a membrane signal corresponding to the acoustic vibrations based at least in part on an attached state of the acoustic sensor;
- a probe-off assembly supported by the sensor support, the probe-off assembly configured to produce a probe-off signal responsive to the attached state of the acoustic sensor and to a detached state of the acoustic sensor; and
- at least one attachment member supported by the sensor support and located in a first position in the detached state of the acoustic sensor and located in a second position in the attached state of the acoustic sensor that is different than the first position,
- wherein the probe-off signal is responsive to movement of the attachment member between the first position and the second position to indicate a change in an integrity of a connection between the acoustic sensor and the medical patient.

12. The acoustic sensor of claim 11, wherein the probe-off assembly further comprises a switch supported by the sensor support, and wherein movement of the at least one attachment member from the first position to the second position actuates the switch.

13. The acoustic sensor of claim 12, further comprising a rigid shell supported by the sensor support, at least a portion of the shell positioned over the switch.

14. The acoustic sensor of claim 11, wherein the attachment member comprises a resilient, elongate member.

15. The acoustic sensor of claim 11, wherein the attachment member extends across the sensor support and beyond opposing sides of the sensor support.

16. The acoustic sensor of claim 11, wherein the attachment member comprises an adhesive adapted to secure the attachment member to the medical patient's skin.

17. The acoustic sensor of claim 11, further comprising a resilient portion supported by the sensor support and arranged to bias the attachment member in the first position in the detached state of the acoustic sensor.

18. The acoustic sensor of claim 17, wherein the resilient portion forms a part of a casing stretched around and encasing at least a portion of the sensor support.

19. A method for determining a connection state between a non-invasive acoustic sensor and a medical patient, the method comprising:
- outputting from a non-invasive acoustic sensor comprising a sensor support and a probe-off assembly, an attachment state signal indicating that the acoustic sensor is in an unattached state based at least in part on at least one attachment member of the acoustic sensor being in a first position, the acoustic sensor further comprising at least one sound sensing membrane configured to detect acoustic vibrations indicative of one or more physiological parameters of the medical patient;
- outputting the attachment state signal from the acoustic sensor indicating that the acoustic sensor is in an attached state based at least in part on the at least one attachment member moving from the first position to a second position, wherein the attachment state signal indicates a change in an integrity of a connection between the acoustic sensor and the medical patient; and
- outputting a data signal from the sensor indicative of the one or more physiological parameters based at least in part on the attachment state signal indicating that the acoustic sensor is in the attached state.

20. An acoustic sensor configured to non-invasively detect a probe-off condition, said acoustic sensor comprising:
- a sensor support;
- a sound sensing device supported by the sensor support and configured to detect acoustic vibrations associated with a medical patient and produce an acoustic signal corresponding to the acoustic vibrations; and
- one or more probe-off elements coupled to at least one of the sensor support or the sound sensing device, the one or more probe-off elements configured to produce a signal indicative of a probe-off condition responsive to the acoustic sensor in a detached state and/or in an attached state, wherein at least a portion of the sensor support is between a patient contact surface of the acoustic sensor and the one or more probe-off elements.

21. The acoustic sensor of claim 20, wherein the one or more probe-off elements comprise a switch configured to actuate in response to attachment of the sensor to the medical patient.

22. The acoustic sensor of claim 20, wherein the one or more probe-off elements comprise two conductive elements applied to one or both of the sensor support and the sound sensing device.

23. The acoustic sensor of claim 22, wherein the two conductive elements comprise conductive films.

24. The acoustic sensor of claim 22, wherein the signal indicative of the probe-off condition comprises a resistance signal measured with respect to the two conductive elements.

25. The acoustic sensor of claim 24, wherein a value of the resistance signal that meets a threshold resistance is configured to indicate the probe-off condition.

26. An acoustic sensor configured to non-invasively detect a probe-off condition, said acoustic sensor comprising:
- a sensor support;
- a sound sensing device supported by the sensor support and configured to detect acoustic vibrations associated with a medical patient and produce an acoustic signal corresponding to the acoustic vibrations; and
- one or more probe-off elements coupled to at least one of the sensor support or the sound sensing device, the one or more probe-off elements configured to produce a signal responsive to the acoustic sensor in a detached state and/or in an attached state, wherein a mechanically active portion of the sound sensing device is configured to move in response to the acoustic vibrations is further configured to be located between the medical patient's skin and the one or more probe-off elements based at least in part on the sensor being in the attached state.

27. An acoustic sensor configured to non-invasively detect a probe-off condition, said acoustic sensor comprising:

a sensor support;

a sound sensing device supported by the sensor support and configured to detect acoustic vibrations associated with a medical patient and produce an acoustic signal corresponding to the acoustic vibrations;

one or more probe-off elements coupled to at least one of the sensor support or the sound sensing device, the one or more probe-off elements configured to produce a signal responsive to the acoustic sensor in a detached state and/or in an attached state; and at least one attachment member supported by the sensor support and located in a first position in the detached state of the acoustic sensor and located in a second position in the attached state of the acoustic sensor that is different than the first position, wherein the signal is responsive to movement of the attachment member between the first position and the second position to indicate a change in an integrity of a connection between the acoustic sensor and the medical patient.

* * * * *